US010952667B2

(12) United States Patent
Oh et al.

(10) Patent No.: US 10,952,667 B2
(45) Date of Patent: Mar. 23, 2021

(54) DEVICE AND METHOD OF CONTROLLING WEARABLE DEVICE

(71) Applicant: Samsung Electronics Co., Ltd., Suwon-si (KR)

(72) Inventors: Ji-heon Oh, Gwacheon-si (KR); Nam-hoon Kim, Suwon-si (KR); Jae-myeon Lee, Yongin-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 273 days.

(21) Appl. No.: 14/980,206

(22) Filed: Dec. 28, 2015

(65) Prior Publication Data
US 2016/0183869 A1    Jun. 30, 2016

(30) Foreign Application Priority Data

Dec. 26, 2014  (KR) .................... 10-2014-0191133
Dec. 15, 2015  (KR) .................... 10-2015-0179207

(51) Int. Cl.
 *A61B 5/00*  (2006.01)
 *A61B 5/11*  (2006.01)
 *A61B 90/00*  (2016.01)

(52) U.S. Cl.
 CPC ............ *A61B 5/486* (2013.01); *A61B 5/1118* (2013.01); *A61B 5/1123* (2013.01); *A61B 5/681* (2013.01);
(Continued)

(58) Field of Classification Search
 CPC ..... A61B 5/486; A61B 5/1118; A61B 5/1123; A61B 5/681; A61B 5/684; A61B 5/743; A61B 5/7475
(Continued)

(56) References Cited

U.S. PATENT DOCUMENTS 8,088,043 B2   1/2012   Andren et al.
8,684,900 B2   4/2014   Tran
(Continued)

FOREIGN PATENT DOCUMENTS

CN   102473025 A   5/2012
WO   2014107629 A1   7/2014

OTHER PUBLICATIONS

Communication with Extended European Search Report dated Dec. 5, 2017 corresponding to European Patent Application No. 15873693.4.

(Continued)

*Primary Examiner* — Daniel L Cerioni
(74) *Attorney, Agent, or Firm* — Nixon & Vanderhye P.C.

(57) ABSTRACT

Provided are a device and method of controlling a wearable device. The device may include a communicator configured to communicate with one or more wearable devices that are worn on a user's body and obtain physical information of the user; and a controller configured to determine wearing positions where the one or more wearable devices are worn on the user's body, to determine a type of activity (e.g., exercise) performed by the user, and to determine, as a main controlled-device based on the wearing positions, at least one wearable device that corresponds to the activity type of the user and is from among the one or more wearable devices worn on the user's body, wherein, via the communicator, the controller controls, from among the one or more wearable devices worn on the user's body, the main controlled-device differently from wearable devices excluding the main controlled-device.

15 Claims, 25 Drawing Sheets

(52) U.S. Cl.
CPC .............. *A61B 5/684* (2013.01); *A61B 5/743* (2013.01); *A61B 5/7475* (2013.01); *A61B 5/0002* (2013.01); *A61B 2090/3612* (2016.02); *A61B 2560/0209* (2013.01)

(58) Field of Classification Search
USPC .......................................................... 600/595
See application file for complete search history.

(56) References Cited

U.S. PATENT DOCUMENTS

| | | |
|---|---|---|
| 8,796,888 B2 | 8/2014 | Rice et al. |
| 2011/0022196 A1 | 1/2011 | Linsky et al. |
| 2011/0275940 A1 | 11/2011 | Nims |
| 2012/0118084 A1 | 5/2012 | Klose et al. |
| 2013/0106684 A1 | 5/2013 | Weast et al. |
| 2013/0147686 A1 | 6/2013 | Clavin et al. |
| 2014/0045547 A1 | 2/2014 | Singamsetty et al. |
| 2014/0135593 A1 | 5/2014 | Jayalth et al. |
| 2014/0135960 A1* | 5/2014 | Choi ................ A61B 5/0205 700/91 |
| 2014/0139486 A1 | 5/2014 | Mistry et al. |
| 2014/0164611 A1 | 6/2014 | Molettiere et al. |
| 2014/0172313 A1 | 6/2014 | Rayner |
| 2014/0278125 A1* | 9/2014 | Balakrishnan ...... G06F 19/3481 702/19 |
| 2014/0310742 A1* | 10/2014 | Kim ..................... H04N 21/485 725/30 |
| 2015/0087995 A1* | 3/2015 | Murai ................... A61B 5/684 600/473 |
| 2015/0317855 A1* | 11/2015 | Sezan ................. A61B 5/1171 340/5.52 |
| 2015/0331598 A1* | 11/2015 | Kang ..................... G06F 3/011 715/765 |
| 2015/0348429 A1* | 12/2015 | Dalal ...................... G09B 5/06 434/258 |
| 2015/0362977 A1* | 12/2015 | Doniwa ............... G06F 1/3231 713/324 |
| 2016/0306422 A1* | 10/2016 | Parham .................. G06F 3/014 |
| 2016/0335557 A1* | 11/2016 | Kurata ................. G06F 1/1626 |
| 2017/0011210 A1* | 1/2017 | Cheong ................ H04W 12/06 |

OTHER PUBLICATIONS

Notification of Transmittal of the International Search Report and the Written Opinion of the International Searching Authority, or the Declaration, International Search Report and Written Opinion of the International Searching Authority dated Apr. 1, 2016 corresponding to International Patent Application PCT/KR2015/014274.

Chinese Office Action dated Sep. 29, 2019 for CN Application No. 201580070891.0.

* cited by examiner

DEVICE AND METHOD OF CONTROLLING WEARABLE DEVICE

RELATED APPLICATION(S)

This application claims the benefit of Korean Patent Application No. 10-2014-0191133, filed on Dec. 26, 2014 and No. 10-2015-0179207, filed on Dec. 15, 2015, in the Korean Intellectual Property Office, the disclosure of which is incorporated herein in its entirety by reference.

BACKGROUND

The present disclosure relates to a device and method of controlling another device, and more particularly, to a device and method of controlling a wearable device that is worn on a user's body so as to obtain physical information of the body.

Recently, various types of wearable devices that may be worn on a user's body are being developed, and functions of the wearable devices are various, thus, each wearable device has a function for sensing a motion of the wearable device or a function for measuring physical variation data of a user.

In this regard, a technique of using the wearable device by interoperating with another device, so that the wearable device worn on a user's body, and the other device interoperating with the wearable device is lacking for convenient use.

SUMMARY

Provided are a device and method of controlling a wearable device that is worn on a user's body so as to obtain physical information about the user's body.

Additional aspects will be set forth in part in the description which follows and, in part, will be apparent from the description, or may be learned by practice of the presented exemplary embodiments.

According to an aspect of an exemplary embodiment, a device includes a communicator configured to communicate with one or more wearable devices that are worn on a user's body and obtain physical information of the user; and a controller configured to determine wearing positions where the one or more wearable devices are worn on the user's body, to determine a type of activity (e.g., exercise) performed by the user, and to determine, as a main controlled-device based on the wearing positions, at least one wearable device that corresponds to the activity type of the user and is from among the one or more wearable devices worn on the user's body, wherein, via the communicator, the controller controls, from among the one or more wearable devices worn on the user's body, the main controlled-device differently from wearable devices excluding the main controlled-device.

The controller may be further configured to display, on the display unit, a screen for recommending activity (e.g., exercise) types corresponding to the wearing positions where the one or more wearable devices are worn on the user's body, and to determine the activity type of the user, based on a user input for selecting at least one of the recommended activity types.

The controller may be further configured to receive movement pattern information of the at least one wearable device for a preset time period via the communicator, and to determine the activity (e.g., exercise) type of the user, based on the received movement pattern information.

The controller may be further configured to control power of the wearable devices to be turned off, wherein the wearable devices exclude the main controlled-device and are from among the one or more wearable devices worn on the user's body.

The controller may be further configured to control the wearable devices to operate in a lower power consumption mode, wherein the wearable devices exclude the main controlled-device and are from among the one or more wearable devices worn on the user's body.

The controller may be further configured to control a physical information obtaining function of the wearable devices to be turned off, wherein the wearable devices exclude the main controlled-device and are from among the one or more wearable devices worn on the user's body.

When a remaining battery power of the main controlled-device is less than a preset reference, the controller may be further configured to re-determine the main controlled-device from among the one or more wearable devices worn on the user's body.

When a wearable device is re-determined as the main controlled-device, the controller may be further configured to control, by using the communicator, the wearable device to obtain physical information of the user.

When a remaining battery power of the main controlled-device is less than a preset reference, the controller may be further configured to control the main controlled-device to output a preset alarm indicating the remaining battery charge.

The device may further include a sensing unit configured to obtain physical information, and the controller may be further configured to control a physical information obtaining function of the sensing unit to be turned off, and to control, via the communicator, the main controlled-device to obtain the physical information of the user.

The device may further include a display unit, and the controller may be further configured to receive, via the communicator, the physical information of the user which is obtained from the main controlled-device, and to display the physical information of the user on the display unit.

The controller may be further configured to display, on the display unit, activity (e.g., exercise) coaching information according to the activity type, based on the physical information of the user.

The device may further include a memory configured to store the wearing positions corresponding to movement patterns of the one or more wearable devices, and the controller may be further configured to receive, via the communicator, a plurality of pieces of movement pattern information of the one or more wearable devices, respectively from the one or more wearable devices worn on the user's body, and to compare the plurality of pieces of movement pattern information with the movement patterns stored in the memory, and to determine the wearing positions that correspond to the plurality of pieces of movement pattern information.

The device may further include a display unit, and the controller may be further configured to display, on the display unit, a screen for guiding a movement pattern for determining the wearing positions of the one or more wearable devices worn on the user's body.

The controller may be further configured to receive, via the communicator, a plurality of pieces of information about the wearing positions of the one or more wearable devices, respectively from the one or more wearable devices worn on the user's body.

The device may further include a camera, and the controller may be further configured to determine the wearing positions where the one or more wearable devices are worn on the user's body, by referring to an image including the user and obtained via the camera.

The device may further include a camera configured to detect a preset spectrum, and the controller may be further configured to detect, by using the camera, a spectrum emitted from the least one wearable device, and to determine, based on the spectrum, a wearing position where the at least one wearable device is worn on the user's body.

According to an aspect of another exemplary embodiment, a device includes a display unit; a communicator configured to communicate with one or more wearable devices that are worn on a user's body and obtain physical information of the user; and a controller configured to determine wearing positions where the one or more wearable devices are worn on the user's body, and to display, on the display unit, a screen for recommending one or more activity (e.g., exercise) types corresponding to the wearing positions, wherein the controller is further configured to receive a user input for selecting at least one of the one or more recommended activity types, and to control, via the communicator, the one or more wearable devices to obtain the physical information of the user according to the at least one selected activity type.

The device may further include a memory configured to store the wearing positions corresponding to movement patterns of the one or more wearable devices, and the controller may be further configured to receive, via the communicator, a plurality of pieces of movement pattern information of the one or more wearable devices, respectively from the one or more wearable devices worn on the user's body, and to compare the plurality of pieces of movement pattern information with the movement patterns stored in the memory, and to determine the wearing positions that correspond to the plurality of pieces of movement pattern information.

The controller may be further configured to display, on the display unit, a screen for guiding a movement pattern for determining the wearing positions of the one or more wearable devices worn on the user's body.

The device may further include a camera, and the controller may be further configured to determine the wearing positions where the one or more wearable devices are worn on the user's body, by referring to an image including the user and obtained via the camera.

The device may further include a camera configured to detect a preset spectrum, and the controller may be further configured to detect, by using the camera, a spectrum emitted from at least one of the one or more wearable devices, and to determine, based on the spectrum, a wearing position where the at least one wearable device is worn on the user's body.

According to an aspect of another exemplary embodiment, a method includes determining wearing positions where one or more wearable devices, which are worn on a user's body and obtain physical information of the user, are worn on the user's body; determining a type of activity (e.g., exercise) performed by the user; determining, as a main controlled-device based on the wearing positions, at least one wearable device that corresponds to the activity type of the user and is from among the one or more wearable devices worn on the user's body; and controlling, by using a communicator, from among the one or more wearable devices worn on the user's body, the main controlled-device differently from wearable devices excluding the main controlled-device.

According to an aspect of another exemplary embodiment, a method includes determining wearing positions where one or more wearable devices, which are worn on a user's body and obtain physical information of the user, are worn on the user's body; displaying, on a display unit, a screen for recommending one or more activity (e.g., exercise) types corresponding to the wearing positions; receiving a user input for selecting at least one of the one or more recommended activity types; and controlling, via a communicator, the one or more wearable devices to obtain the physical information of the user according to the at least one selected activity type.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
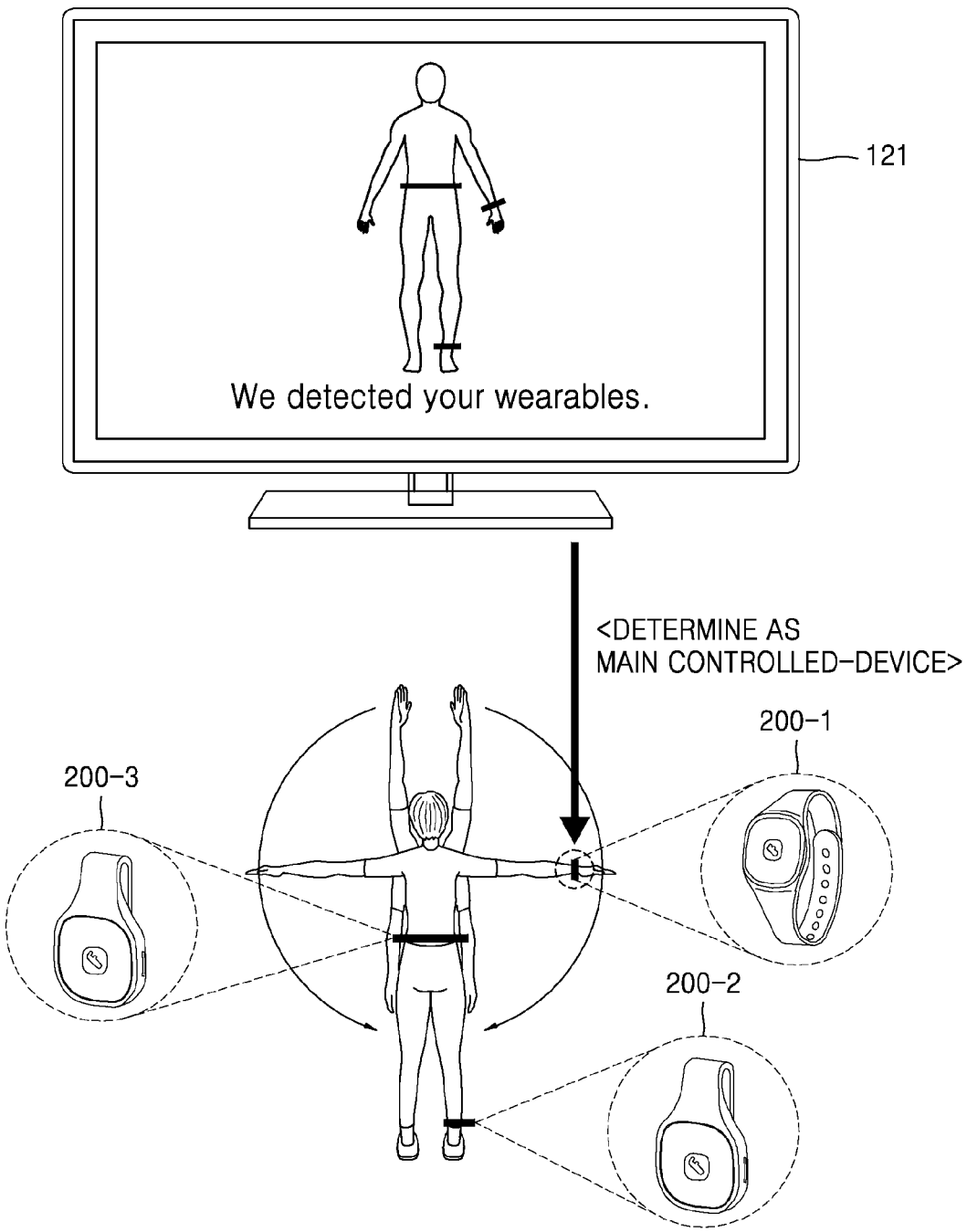
FIG. 1 illustrates a first exemplary embodiment.

Hereinafter, the inventive concept will now be described more fully with reference to the accompanying drawings, in which exemplary embodiments are shown. The inventive concept may, however, be embodied in many different forms and should not be construed as being limited to the exemplary embodiments set forth herein; rather, these exemplary embodiments are provided so that the inventive concept will be thorough and complete, and willfully convey the concept to one of ordinary skill in the art. In the drawings, for a more clear description of the inventive concept, parts or units that are not related to the inventive concept are omitted. Throughout the specification, like reference numerals in the drawings denote like elements.

Advantages and features of the inventive concept may be understood more readily by reference to the following detailed description of exemplary embodiments and the accompanying drawings. The inventive concept may, however, be embodied in many different forms and hereinafter, reference will now be made in detail to exemplary embodiments, examples of which are illustrated in the accompanying drawings, wherein like reference numerals refer to like elements throughout. In the following description, well-known functions or constructions are not described in detail since they would obscure the inventive concept with unnecessary detail. Throughout the specification, the terms "first" and "second" are used only to distinguish between each component.

Hereinafter, an electronic device related to one or more exemplary embodiments is described in detail with reference to the attached drawings. In the following description, terms such as "module" and "unit" that are used for elements do not have their own meanings or functions.

Throughout the specification, a device may include a fixed terminal such as a digital television (TV), a desktop computer, or the like, and a mobile terminal such as a smartphone, a tablet personal computer (PC), a laptop computer, a terminal for digital broadcasting, a personal digital assistant (PDA), a portable multimedia player (PMP), navigation, or the like.

Throughout the specification, it will also be understood that when an element is referred to as being "connected to" or "coupled with" another element, it can be directly connected to or coupled with the other element, or it can be electrically connected to or coupled with the other element by having an intervening element interposed therebetween. Also, when a part "includes" or "comprises" an element, unless there is a particular description contrary thereto, the part can further include other elements, not excluding the other elements.

As used herein, the term "and/or" includes any and all combinations of one or more of the associated listed items. Expressions such as "at least one of," when preceding a list of elements, modify the entire list of elements and do not modify the individual elements of the list.

The term 'physical information' may include information about physical variation data based on movement of a user. For example, the physical information may include a heart rate, calorie consumption, blood pressure, blood flow, a body fat percentage, an electrocardiogram, a muscle mass index, a stress index, or the like. For example, the physical information may include the number of steps, the number of activity (e.g., exercise) repetitions, a movement distance, a movement time, or the like.

A wearable device 200 may indicate an electronic device that is wearable on a user's body and may be embodied in various forms such as a watch, a bracelet, a ring, a necklace, a pendant, a clip, a patch, a tattoo, a contact lens, eyewear, earphones, shoes, or the like, but a form of the wearable device 200 is not limited thereto. Alternatively, the wearable device 200 may be embodied in a same form as described above and may be combined with attachment equipment formed as a band, a patch, a clip, or the like, so that the wearable device 200 may be worn on various parts of the body.

When a user repeats a movement with a particular pattern while the wearable device 200 is worn on a user's body, information about a movement pattern may indicate information including a direction, a speed, an angle, the number of times, or the like that are related to movement of the wearable device 200.

A main controlled-device may indicate a device that is selected, by a device 100, from among one or more wearable devices 200 worn on a user's body, wherein the selected device is worn on a part of the body which is appropriate so as to obtain physical information according to a type of activity (e.g., exercise) performed by the user.

Hereinafter, the inventive concept will now be described more fully with reference to the accompanying drawings.

According to an exemplary embodiment, when a user walks while wearing the wearable devices 200 on his/her wrist and ankle, respectively, the wearable devices 200 may measure the number of his/her steps, calorie consumption, or the like. The device 100 according to an exemplary embodiment may obtain, from a communicator 150 (refer to FIG. 19), user's physical information including the number of his/her steps, the calorie consumption, or the like measured by the wearable devices 200.

Here, in order to further accurately obtain the physical information and to efficiently control a plurality of wearable devices, the device 100 may selectively control a wearable device worn on a part of the body, which is appropriate so as to obtain the physical information of the user according to a type of activity (e.g., exercise) performed by the user. According to an exemplary embodiment, the device 100 may selectively control a plurality of the wearable devices 200 worn on the user's body and thus may create a low power consumption management effect that prevents unnecessary power consumption.

FIG. 1 illustrates a first exemplary embodiment.

Referring to FIG. 1, when a user does arm activity (e.g., exercise) while the user wears a first wearable device 200-1 on his/her wrist, wears a second wearable device 200-2 on his/her ankle, and wears a third wearable device 200-3 on his/her waist, the device 100 may select the first wearable device 200-1 as a main controlled-device, wherein the first wearable device 200-1 is more appropriate for measuring physical information according to arm movement by the user.

Figure 2:
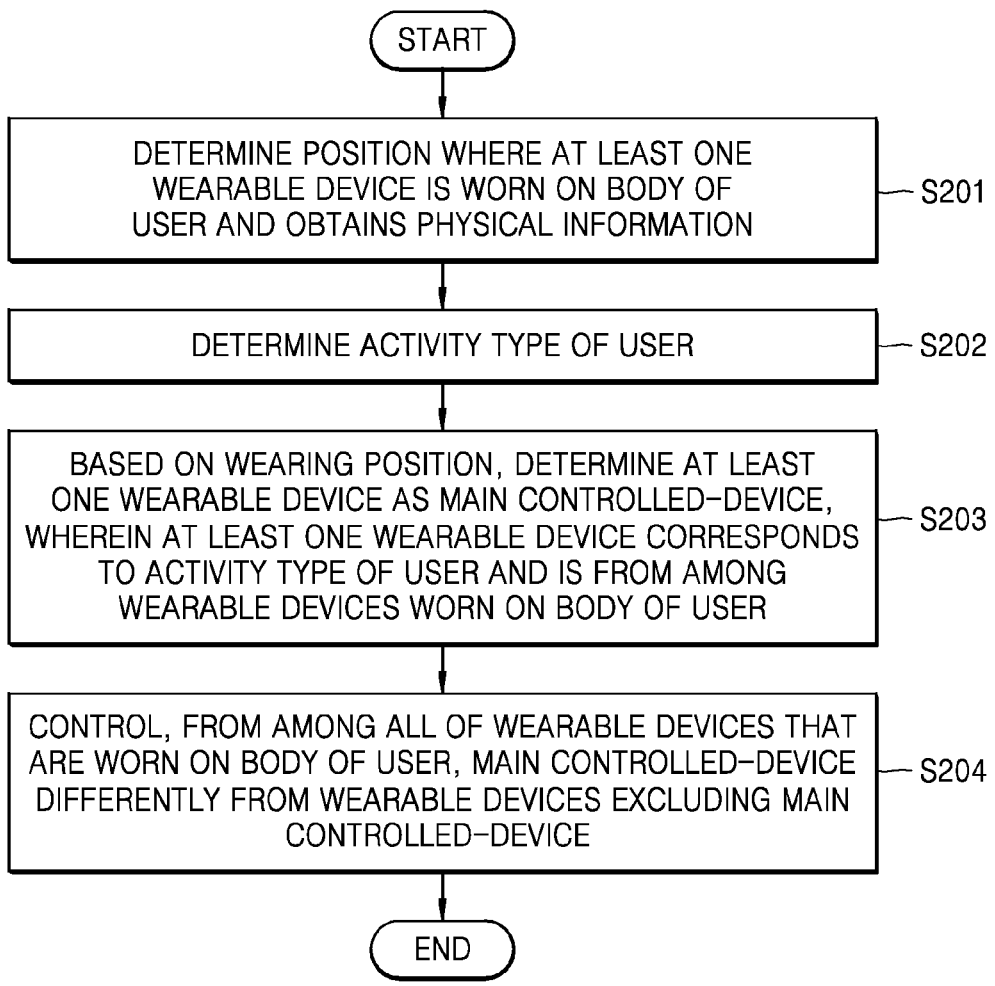
FIG. 2 is a flowchart illustrating the first exemplary embodiment.

FIG. 2 is a flowchart illustrating the first exemplary embodiment.

In operation S201 of FIG. 2, a controller 130 (refer to FIG. 19) of the device 100 may determine a wearing position at which at least one wearable device that is worn on a user's body and obtains physical information is worn on the user's body.

The controller 130 of the device 100 according to the present exemplary embodiment may determine a wearing position of the wearable device 200, based on a movement pattern of the wearable device 200. For example, the device 100 may receive, from the wearable device 200 via the communicator 150, information about the movement pattern which includes a direction, a speed, an angle, or the like that are related to movement of the wearable device 200 that the user wears. Based on the received information about the movement pattern of the wearable device 200, the device 100 may determine that the user has worn the wearable device 200 on his/her arm.

The controller 130 may receive information about the wearing position from the wearable device 200 via the communicator 150.

For example, the wearable device 200 may obtain, via a sensing unit 240 (refer to FIG. 21), the movement pattern including a direction, a speed, an angle, or the like related to movement of the wearable device 200, and may determine the wearing position according to the movement pattern. Also, the wearable device 200 may transmit information about the wearing position determined by the wearable device 200, to the device 100 via a communicator 250. When the wearable device 200 is preset to be worn on a particular part of the body, the wearable device 200 may transmit information about a wearing position to the device 100 via the communicator 250.

The controller 130 may determine a position at which the wearable device 200 is worn on the user's body, by referring to an image that is obtained by a camera 161 (refer to FIG. 19) and includes the user.

The controller 130 may detect, via the camera 161, a spectrum emitted from the wearable device 200, and may determine the position at which the wearable device 200 is worn on the user's body.

Hereinafter, in descriptions with reference to FIGS. 3 through 6, examples in which a wearing position of a wearable device is determined are more fully described.

In operation S202 of FIG. 2, the controller 130 of the device 100 may determine an activity (e.g., exercise) type of the user.

The controller 130 of the device 100 according to the present exemplary embodiment may determine the activity type of the user, based on a user input. For example, based on a user input for selecting an activity type (e.g., arm exercise) from among recommended activity programs provided by the controller 130, the activity type may be determined.

The user may directly input a preset activity type (e.g., a sit-up).

The controller 130 may determine the activity type of the user, based on the information about the movement pattern of the wearable device 200. For example, the device 100 may receive, from the wearable device 200 via the communicator 150, the information about the movement pattern which includes the direction, the speed, the angle, or the like that are related to the movement of the wearable device 200 that the user wears. Based on the received information about the movement pattern of the wearable device 200, the device 100 may determine which activity (e.g., exercise) the user is doing, i.e., the activity type (e.g., the arm exercise) of the user.

Hereinafter, in descriptions with reference to FIGS. 7 through 9, examples in which the activity type of the user is determined are more fully described.

In operation S203 of FIG. 2, based on wearing positions at which wearable devices are worn on the user's body, the controller 130 of the device 100 may determine at least one wearable device as a main controlled-device, wherein the at least one wearable device corresponds to the activity (e.g., exercise) type of the user and is from among the wearable devices worn on the user's body.

For example, while the user wears wearable devices on his/her wrist and ankle, respectively, when the controller 130 of the device 100 determines the arm activity as the activity type of the user, the controller 130 of the device 100 may determine the wearable device, which is worn on the wrist, as the main controlled-device.

In operation S204 of FIG. 2, the device 100 may differently control, from among the wearable devices that are worn on the user's body, the main controlled-device from wearable devices excluding the main controlled-device.

The controller 130 of the device 100 according to the present exemplary embodiment may control power of the wearable devices to be turned off, wherein the wearable devices exclude the main controlled-device and are from among the wearable devices that are worn on the user's body.

For example, the device 100 turns off the power of the wearable device worn on the ankle which is not appropriate for measuring an amount of activity, physical variation of the body, or the like according to the arm activity performed by the user, and by doing so, the device 100 may prevent unnecessary power consumption and may create a low power consumption management effect.

Figure 3:
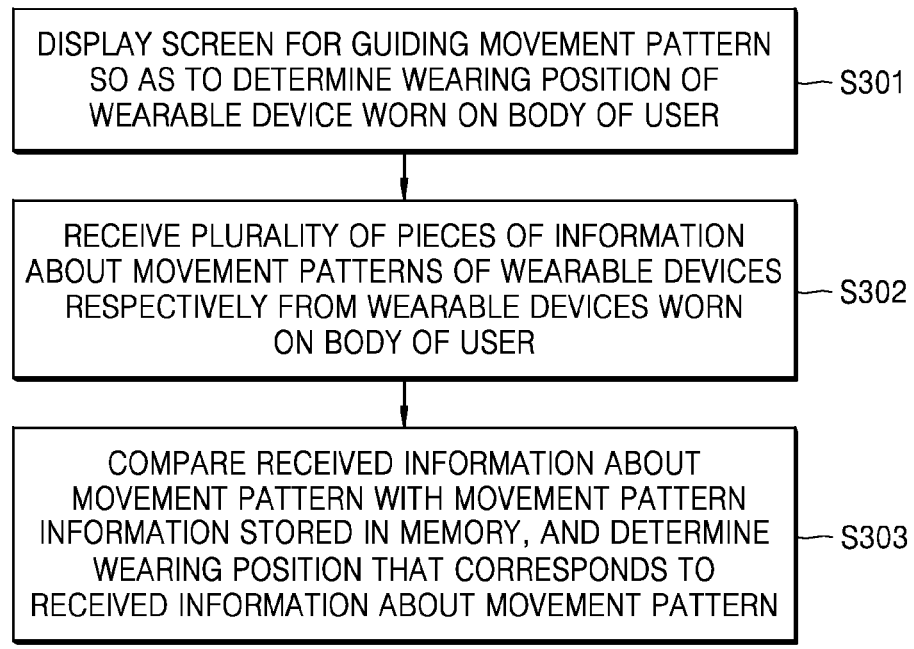
FIG. 3 is a flowchart illustrating an example in which a wearing position of a wearable device is determined, according to an exemplary embodiment.
Figure 4:
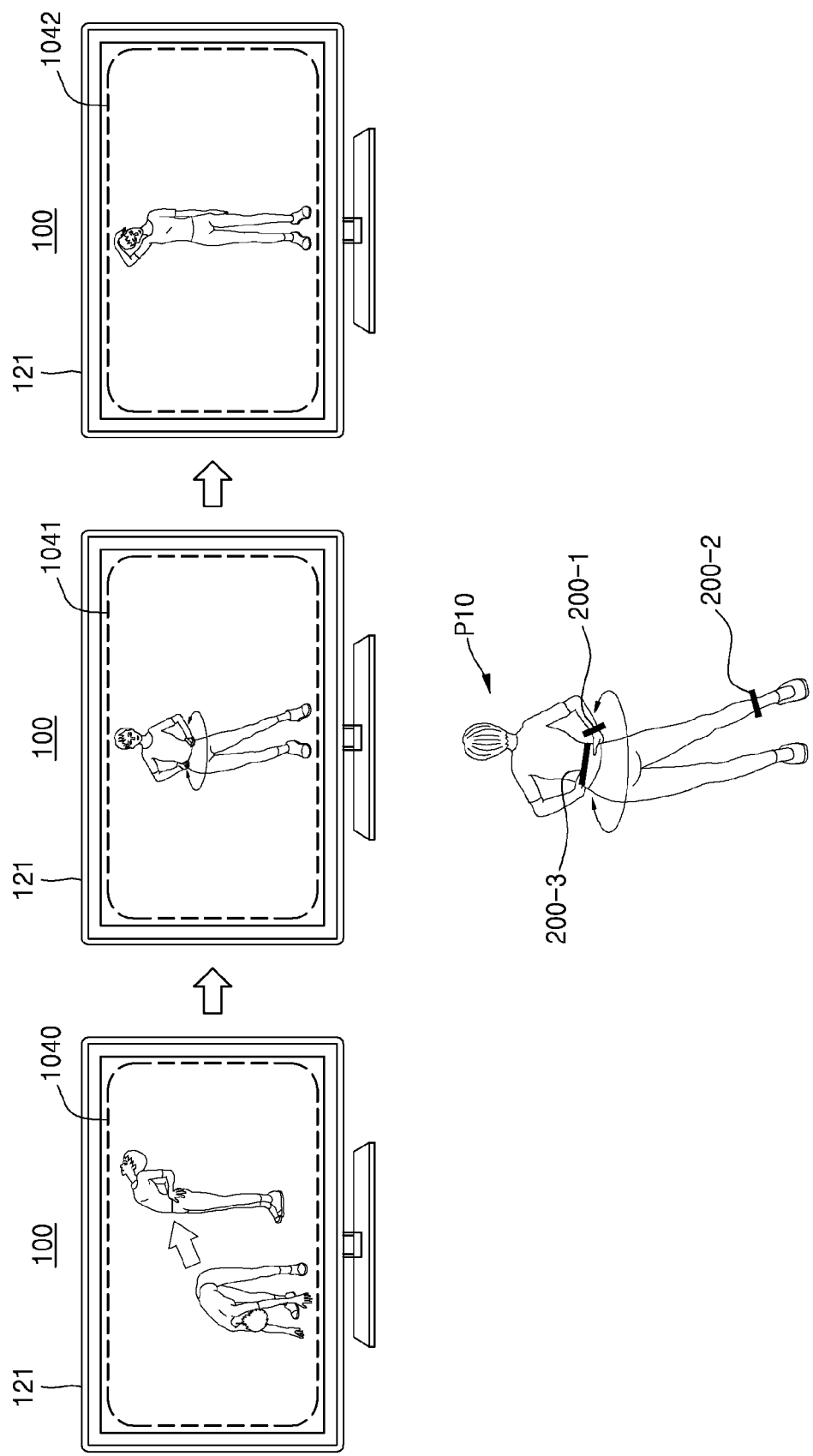
FIG. 4 illustrates the example in which the wearing position of the wearable device is determined, according to the exemplary embodiment.

FIG. 3 is a flowchart illustrating an example in which a wearing position of a wearable device is determined, according to an exemplary embodiment. FIG. 4 illustrates the example in which the wearing position of the wearable device is determined, according to the exemplary embodiment.

According to an exemplary embodiment, when a user moves according to a warming-up activity pattern provided on a display unit 121 (refer to FIG. 19) of the device 100, the device 100 may determine a wearing position such as an arm, a leg, or the like, based on a movement pattern of the user who wears the wearable device 200.

In operation S301 of FIG. 3, the device 100 may display a screen for guiding a movement pattern so as to determine the wearing position of the wearable device that is worn on a user's body.

For example, as illustrated in FIG. 4, the controller 130 of the device 100 may display, on the display unit 121, warming-up activity (e.g., exercise) screens 1040, 1041, and 1042 so as to guide a user P10 to warming-up activity.

In operation S302 of FIG. 3, the device 100 may receive a plurality of pieces of information about movement patterns of wearable devices respectively from the wearable devices worn on the user's body.

Figure 21:
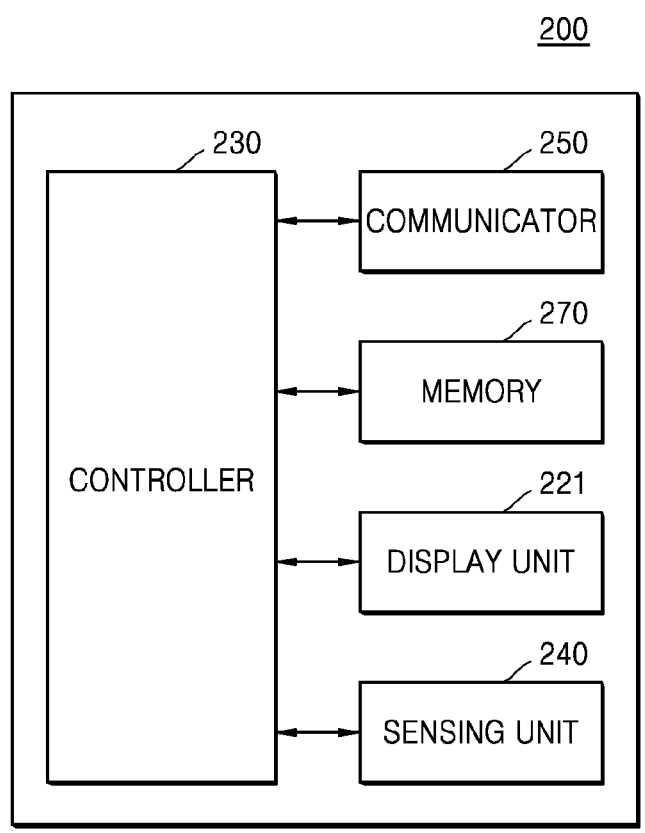
FIG. 21 is a block diagram of a wearable device, according to an exemplary embodiment.

For example, as illustrated in FIG. 4, when the user p10 moves according to the warming-up activity (e.g., exercise) displayed on the display unit 121, each of the first, second, and third wearable devices 200-1, 200-2, and 200-3 worn on the user's body may obtain a movement pattern of the user by using the sensing unit 240, and may transmit the movement pattern to the device 100 via a communicator 250 (refer to FIG. 21).

In operation S303 of FIG. 3, the device 100 may compare the received information about the movement pattern with movement pattern information stored in a memory, and may determine a wearing position that corresponds to the received information about the movement pattern.

The device 100 may previously store, in a memory 170 (refer to FIG. 19), movement pattern information with respect to each of wearing positions of the wearable device 200 for a case in which the user wears the wearable device 200 and moves according to warming-up activity provided by the device 100. The movement pattern information may include information about an angle, a speed, a direction, or the like that are related to a movement at each of the wearing positions of the wearable device 200.

For example, the memory 170 may previously store movement pattern information about a case in which the user wears the wearable device 200 on his/her wrist and does arm warming-up activity (e.g., exercise) provided by the device 100. When the received information about the movement pattern of the user matches the stored movement pattern information, the controller 130 may determine the wrist as the wearing position.

Figure 5:
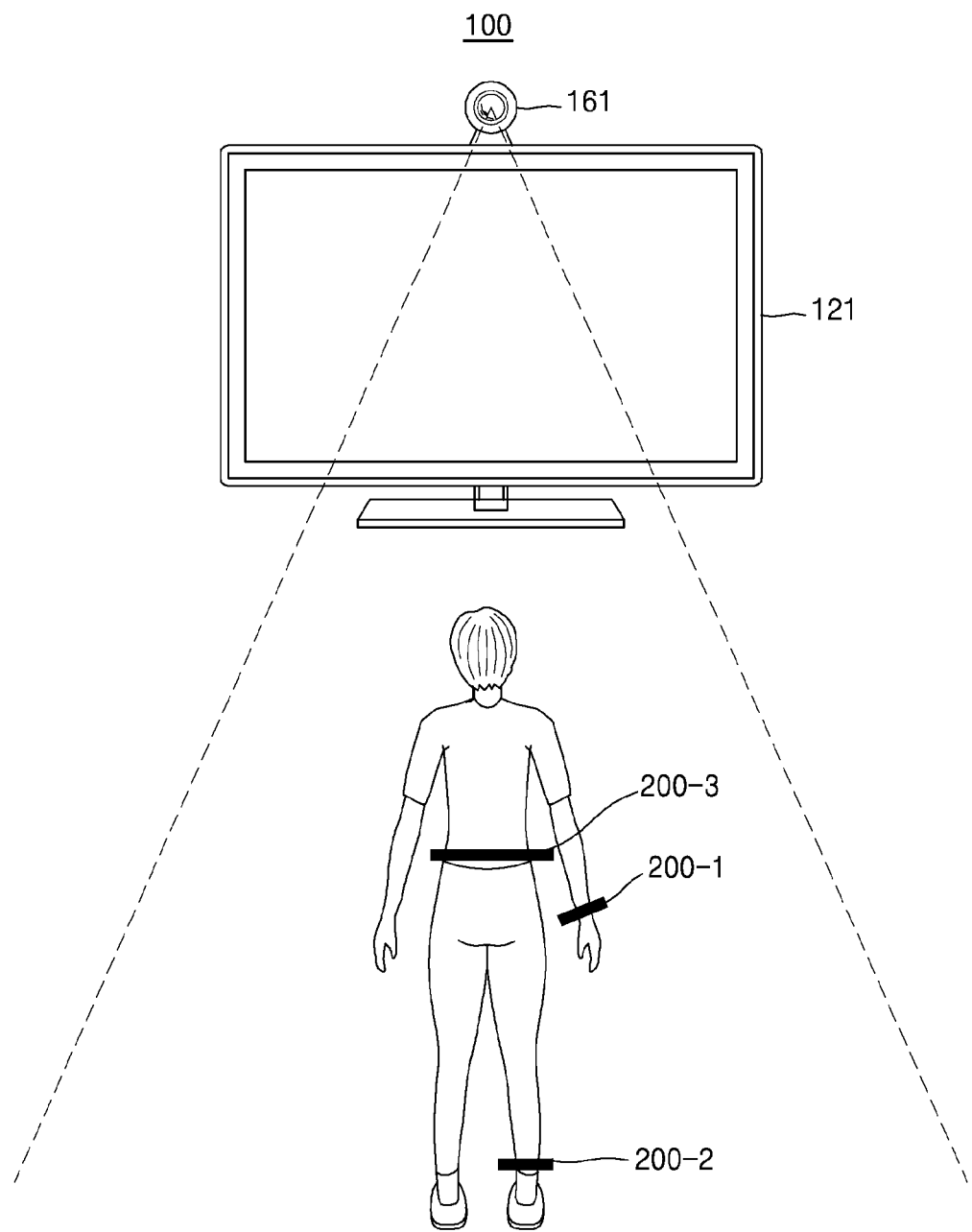
FIG. 5 illustrates an example in which a wearing position of a wearable device is determined, according to another exemplary embodiment.

FIG. 5 illustrates an example in which a wearing position of a wearable device is determined, according to another exemplary embodiment.

According to the present exemplary embodiment, the device 100 may obtain an image, that may include a user, via the camera 161 mounted in the device 100. The controller 130 of the device 100 may extract the wearing position of the wearable device from the image.

For example, as illustrated in FIG. 5, when the user wears the first, second, and third wearable devices 200-1, 200-2, and 200-3 and positions in a direction of the camera 161 of the device 100, the controller 130 may capture an image of the user by using the camera 161. The controller 130 of the device 100 may determine, by using a preset object recognition algorithm, positions of the first, second, and third wearable devices 200-1, 200-2, and 200-3 included in the captured image.

According to the present exemplary embodiment, the controller 130 may recognize a face of the user in the image including the user and obtained via the camera 161, and may apply an identification number to the user. For example, the controller 130 may apply identification numbers respectively to a plurality of users in the image, and may store a plurality of pieces of user information, based on the identification numbers respectively applied to the users. Each of the plurality of pieces of user information may include a history of activity types of each user, physical information of each user, a history of fitness information of each user, or the like.

According to the present exemplary embodiment, the controller 130 may recommend an activity (e.g., exercise) type, based on the user information of the recognized user. For example, the controller 130 may provide activity coaching information, based on the user information of the recognized user.

Figure 6:
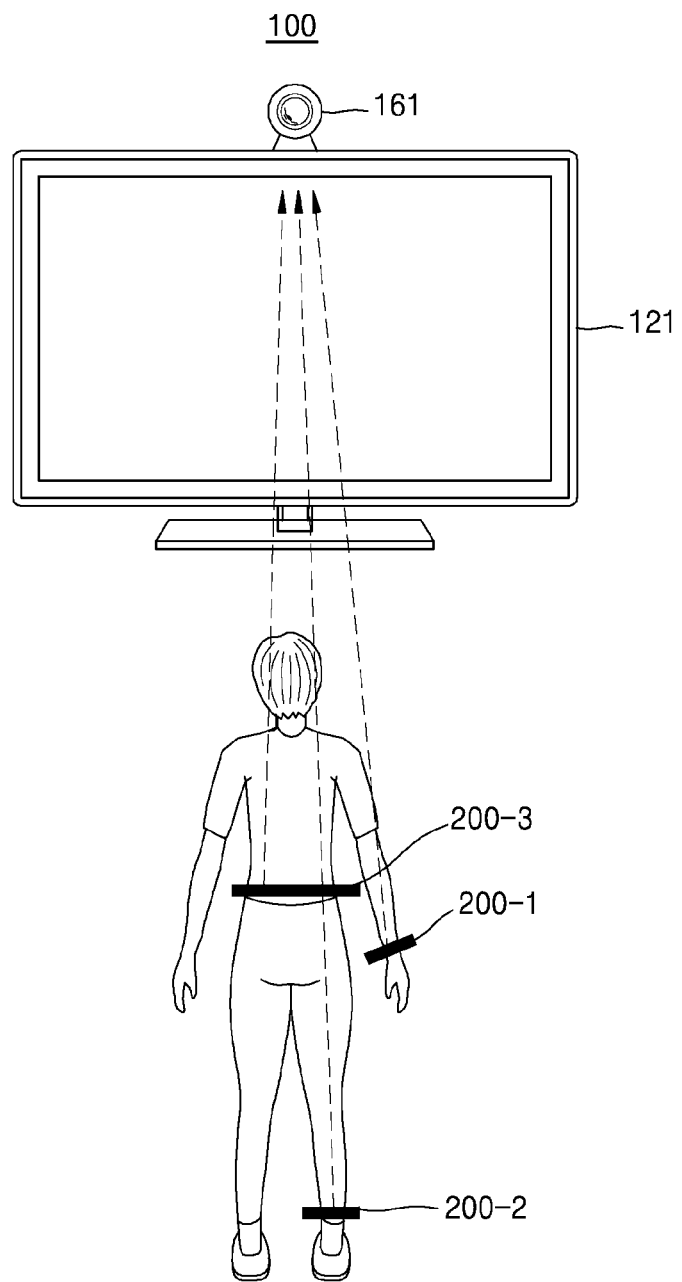
FIG. 6 illustrates an example in which a wearing position of a wearable device is determined, according to another exemplary embodiment.

FIG. 6 illustrates an example in which a wearing position of a wearable device is determined, according to another exemplary embodiment.

According to the present exemplary embodiment, the device 100 may include the camera 161 that detects a predetermined spectrum (e.g., infrared rays, ultraviolet rays, etc.). Also, the wearable device 200 may include an apparatus (not shown) for emitting the predetermined spectrum (e.g., infrared rays, ultraviolet rays, etc.).

For example, as illustrated in FIG. 6, when the user wears the first, second, and third wearable devices 200-1, 200-2, and 200-3 and positions in front of the camera 161 of the device 100, the camera 161 of the device 100 may detect a spectrum emitted from each of the first, second, and third wearable devices 200-1, 200-2, and 200-3 and thus may determine wearing positions of the first, second, and third wearable devices 200-1, 200-2, and 200-3.

Figure 7:
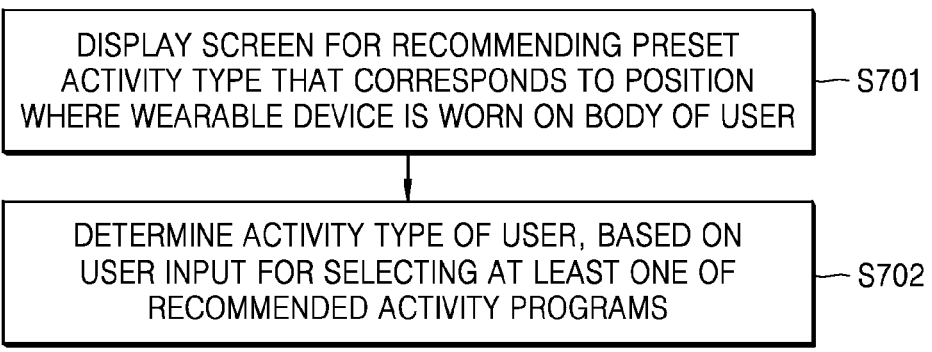
FIG. 7 is a flowchart illustrating an example in which an activity (e.g., exercise) type of a user is determined, according to an exemplary embodiment.

FIG. 7 is a flowchart illustrating an example in which an activity (e.g., exercise) type of a user is determined, according to an exemplary embodiment. FIG. 8 illustrates the example in which the activity type of the user is determined, according to the exemplary embodiment.

In operation S701 of FIG. 7, the controller 130 of the device 100 may display, on the display unit 121, a screen for recommending a preset activity type that corresponds to a position at which the wearable device 200 is worn on a user's body.

Figure 8:
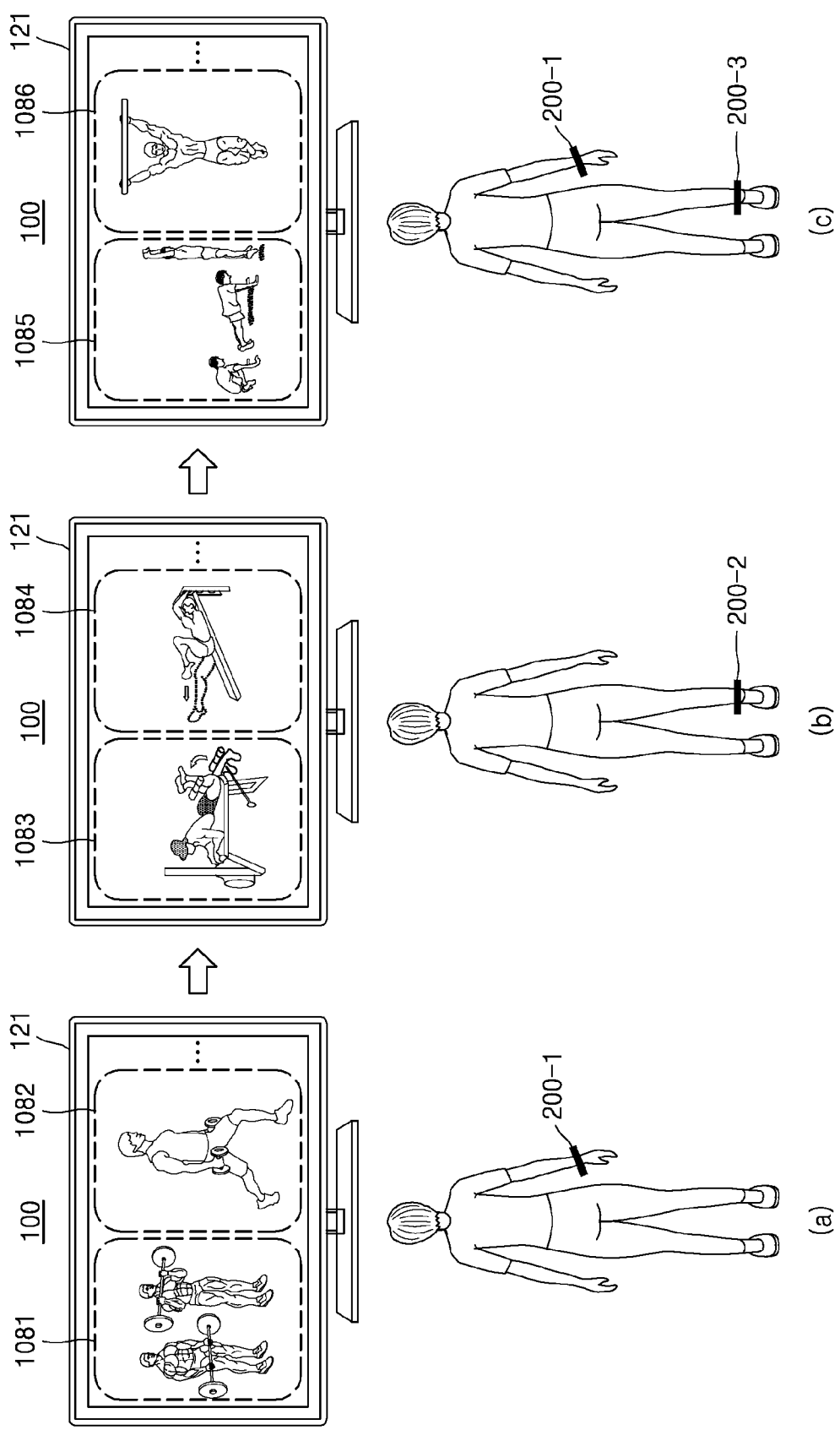
FIG. 8 illustrates the example in which the activity (e.g., exercise) type of the user is determined, according to the exemplary embodiment.

As illustrated in an exemplary embodiment of (a) of FIG. 8, when the controller 130 of the device 100 determines that the user wears the first wearable device 200-1 at his/her wrist, the controller 130 of the device 100 may provide, on the display unit 121, screens 1081 and 1082 for recommending an activity (e.g., exercise) program (e.g., barbell curls, push-ups, etc.) in which the user mainly uses hands or arms.

Referring to an exemplary embodiment of (b) of FIG. 8, when the controller 130 of the device 100 determines that the user wears the second wearable device 200-2 at his/her ankle, the controller 130 of the device 100 may provide, on the display unit 121, screens 1083 and 1084 for recommending an activity (e.g., exercise) program in which the user mainly uses feet or legs.

Referring to an exemplary embodiment of (c) of FIG. 8, when the controller 130 of the device 100 determines that the user wears the first and second wearable device 200-1 and 200-2 at his/her wrist and ankle, the controller 130 of the device 100 may provide, on the display unit 121, screens 1085 and 1086 for recommending an activity (e.g., exercise) program in which the user mainly uses hands, arms, feet and legs.

In operation S702 of FIG. 7, the device 100 may determine an activity (e.g., exercise) type of the user, based on a user input for selecting at least one of the recommended activity programs.

For example, in a case where the user wears a wearable device on the wrist and thus the controller 130 recommends a push-up exercise program and a barbell curl exercise program, when the user selects the barbell curl exercise program, the controller 130 may determine the barbell curl exercise program as the exercise type.

When the display unit 121 is formed as a touch screen, the user input with respect to the selection may be a user's touch input with respect to the touch screen. The controller 130 may receive, via short-distance communication, a control signal from an external device (e.g., a remote controller) that controls the device 100.

The device 100 may display, on the display unit 121, bar codes or quick response (QR) codes which correspond to the recommended activity (e.g., exercise) programs. For example, the user may scan, by using the wearing wearable device 200, a bar code or a QR code that corresponds to a selection-target activity program, and the device 100 may receive the user input with respect to the selection by receiving scanned information. The user input with respect to the selection is not limited thereto.

Figure 9:
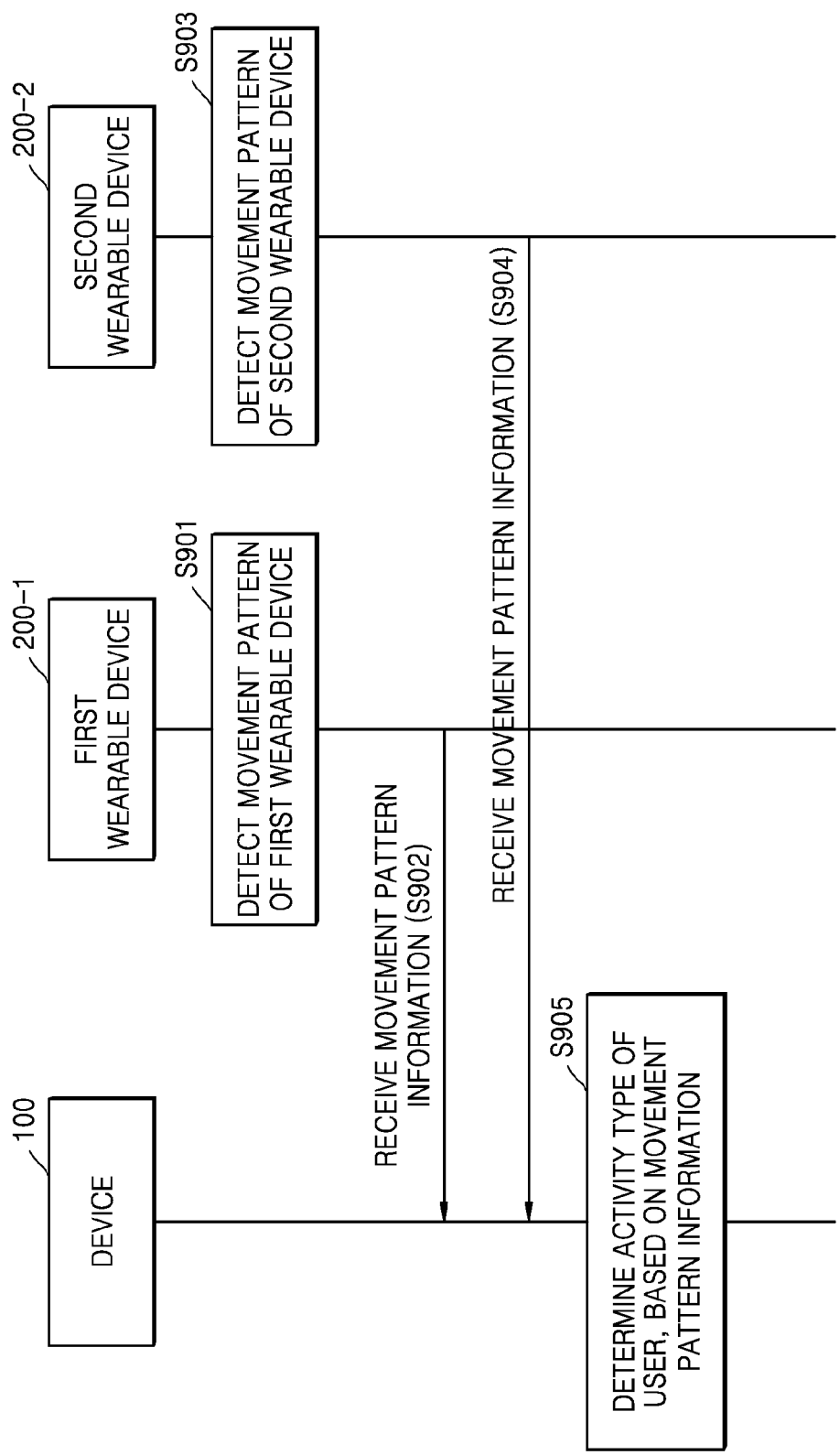
FIG. 9 is a flowchart illustrating an example in which an activity (e.g., exercise) type of a user is determined, according to another exemplary embodiment.

FIG. 9 is a flowchart illustrating an example in which an activity type of a user is determined, according to another exemplary embodiment.

In operation S901 of FIG. 9, the first wearable device 200-1 may detect a movement pattern of the first wearable device 200-1. In operation S903 of FIG. 9, the second wearable device 200-2 may detect a movement pattern of the second wearable device 200-2.

For example, the first and second wearable devices 200-1 and 200-2 may sense movements of the first and second wearable devices 200-1 and 200-2, respectively, by using a magnetic sensor, an acceleration sensor, a proximity sensor, a gyroscope sensor, a position sensor, or the like that is located or embedded in or on each of the first and second wearable devices 200-1 and 200-2, and may obtain movement pattern information by measuring a movement direction, a speed, a change in the speed, or the like.

In operation S902 of FIG. 9, the device 100 may receive the movement pattern information from the first wearable device 200-1. In operation S904, the device 100 may receive the movement pattern information from the second wearable device 200-2.

The device 100 may receive, via the communicator 150, wearable device movement pattern information from each of the first and second wearable devices 200-1 and 200-2 that are worn on a user's body.

In operation S905, the device 100 may determine an activity (e.g., exercise) type of the user, based on the wearable device movement pattern information. That is, the controller 130 of the device 100 may automatically determine which activity (e.g., exercise) the user is doing, based on the movement pattern information including a direction, a speed, an angle, or the like related to a movement of each of the first and second wearable devices 200-1 and 200-2.

Figure 10A:
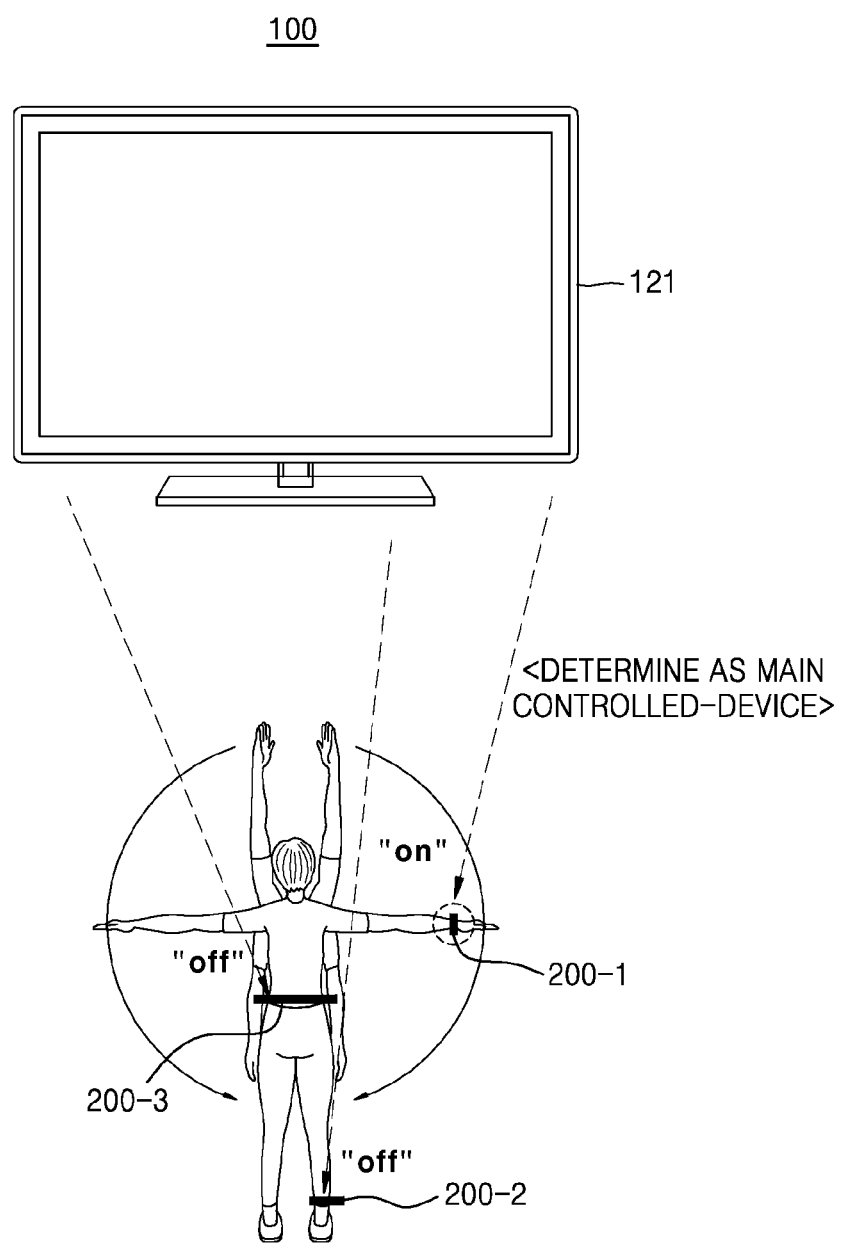
FIG. 10A illustrates an example in which a wearable device is controlled, according to an exemplary embodiment
Figure 10B:
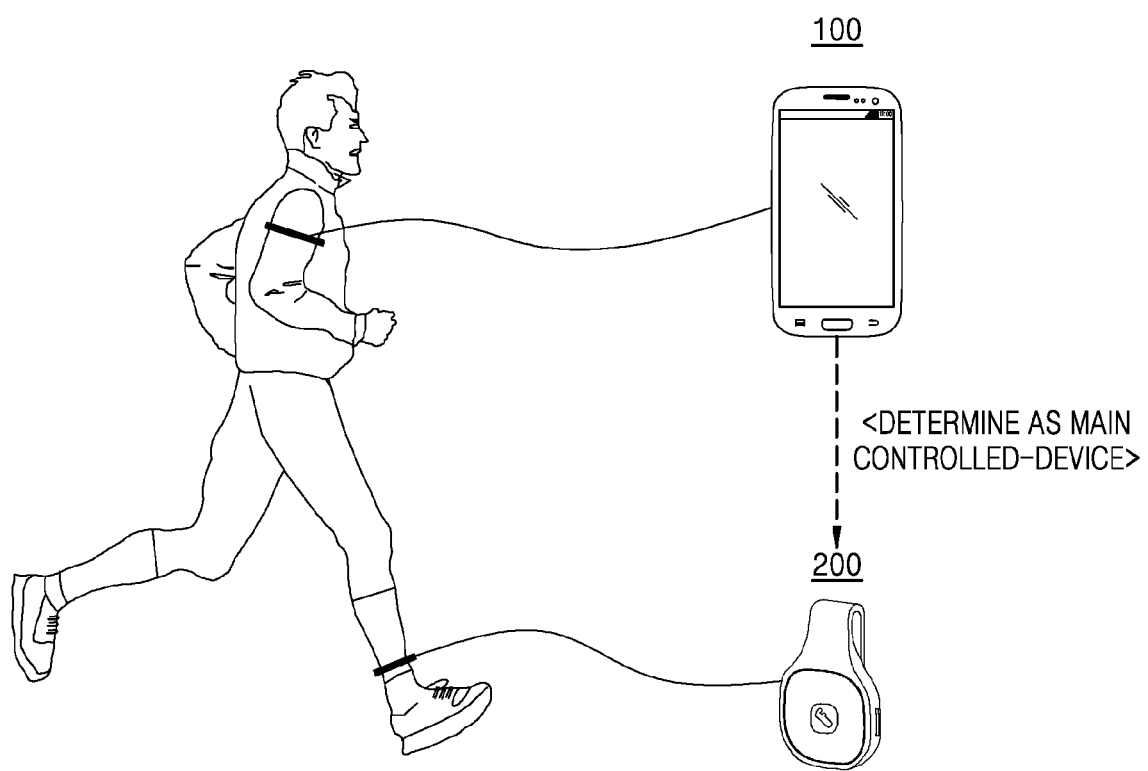
FIG. 10B illustrates another example in which a wearable device is controlled, according to an exemplary embodiment.

FIGS. 10A and 10B illustrate an example in which a wearable device is controlled, according to an exemplary embodiment.

As illustrated in FIG. 10A, the device 100 according to the present exemplary embodiment may determine, as a main controlled-device, the first wearable device 200-1 from among the first, second, and third wearable devices 200-1, 200-2, and 200-3 that are worn on a user's body.

Also, the controller 130 of the device 100 may differently control, from among the first, second, and third wearable devices 200-1, 200-2, and 200-3 that are worn on the user's body, the main controlled-device 200-1 from the second and third wearable devices 200-2 and 200-3 excluding the main controlled-device 200-1.

For example, when the user is doing arm activity (e.g., exercise), the controller 130 of the device 100 may determine, as a main controlled-device, the first wearable device 200-1 that is worn on a wrist appropriate for measuring an amount of activity (e.g., exercise) according to the arm activity (e.g., exercise). Here, the controller 130 may control power of the second and third wearable devices 200-2 and 200-3, while excluding the main controlled-device 200-1, to be turned off.

The controller 130 may also control a physical information obtaining function of the second and third wearable devices 200-2 and 200-3, while excluding the main controlled-device 200-1, to be turned off.

For example, the physical information obtaining function of the sensing unit 240, which is in each of the second and third wearable devices 200-2 and 200-3, may be turned off, so that battery consumption of the wearable device 200 may be significantly reduced.

The controller 130 may control the second and third wearable devices 200-2 and 200-3, while excluding the main controlled-device 200-1, to operate in a low power consumption mode. The low power consumption mode may indicate a mode in which all functions except for preset fewest functions are turned off so as to significantly reduce battery consumption. During the low power consumption mode, the physical information obtaining function of each of the second and third wearable devices 200-2 and 200-3 may be turned off. Referring to FIG. 10A, according to an exemplary embodiment, while the user is doing the arm activity (e.g., exercise), a movement of the second wearable device 200-2 worn on an ankle of the user and a movement of the third wearable device 200-3 worn on a waist of the user may be small, and thus may not be appropriate for measuring physical variation. Therefore, the device 100 may differently control the first wearable device 200-1 from the second wearable device 200-2 that is worn on the ankle of the user and the third wearable device 200-3 that is worn on the waist of the user, and thus may create an effect of efficiently managing the plurality of wearable devices by using lower power consumption.

FIG. 10B illustrates an example in which the device 100 has a function capable of obtaining physical information of a user. According to an exemplary embodiment, the device 100 may include a sensing unit 140 (refer to FIG. 20) that obtains information about variation of a body according to a movement of a user and information about an amount of activity (e.g., exercise) according to the movement. For example, referring to FIG. 10B, the device 100 may measure the number of steps of a user by using the sensing unit 140.

As illustrated in FIG. 10B, the user may attach the device 100 (e.g., a smartphone) on an arm, and may wear the wearable device 200 on a shoe. Here, if the user is doing jogging, the device 100 in the form of a smartphone may determine the wearable device 200, which is attached to the shoe of the user, as a main controlled-device.

The device 100 in the form of a smartphone may control, via the communicator 150, the wearable device 200 determined as the as main controlled-device to obtain the number of steps of the user. The device 100 in the form of a smartphone may receive, via the communicator 150, information about the number of steps of the user which is obtained from the wearable device 200.

In this case, the controller 130 of the device 100 may turn off a step-counting function of the device 100. Also, the device 100 may switch a mode of the device 100 to a low power consumption mode. By doing so, the device 100 may create a low power consumption management effect.

When the user has a plurality of devices (e.g., the device 100 and the wearable device 200), a device at a wearing position which is more appropriate for measuring the number of steps of the user may be selected from among the plurality of devices, so that the number of steps may be more accurately measured.

Figure 11:
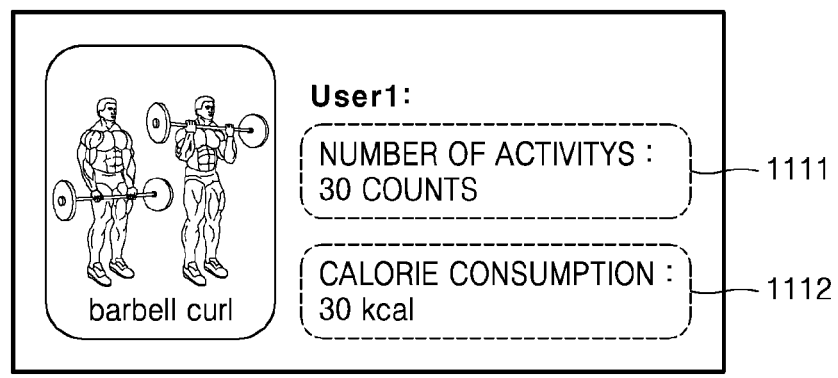
FIG. 11 illustrates an example in which physical information obtained from a wearable device is displayed, according to an exemplary embodiment.

FIG. 11 illustrates an example in which physical information obtained from a wearable device is displayed, according to an exemplary embodiment.

The controller 130 of the device 100 according to an exemplary embodiment may receive, via the communicator 150, physical information of a user which is obtained from a main controlled-device (e.g., the wearable device 200), and may display the received physical information of the user on the display unit 121.

For example, as illustrated in FIG. 11, when the user does a barbell curl exercise, the controller 130 may receive information about the number of exercises (e.g., "number of exercises: 30 counts" 1111) from the wearable device 200 worn on a user's body, and may provide the information to the display unit 121.

The controller 130 may receive information about calorie consumption (e.g., "calorie consumption: 30 kcal" 1112) from the wearable device 200 worn on the user's body, and may provide the information to the display unit 121.

According to the present exemplary embodiment, the controller 130 may store and manage a plurality of pieces of physical information with respect to a plurality of users, based on a plurality of pieces of identification information for identifying the users.

The controller 130 may identify the users by recognizing faces of the users via the camera 161, and may apply, to the users, the plurality of pieces of identification information that correspond to the users, respectively. In addition, the controller 130 may receive the identification information of the user from the wearable device 200.

Figure 12:
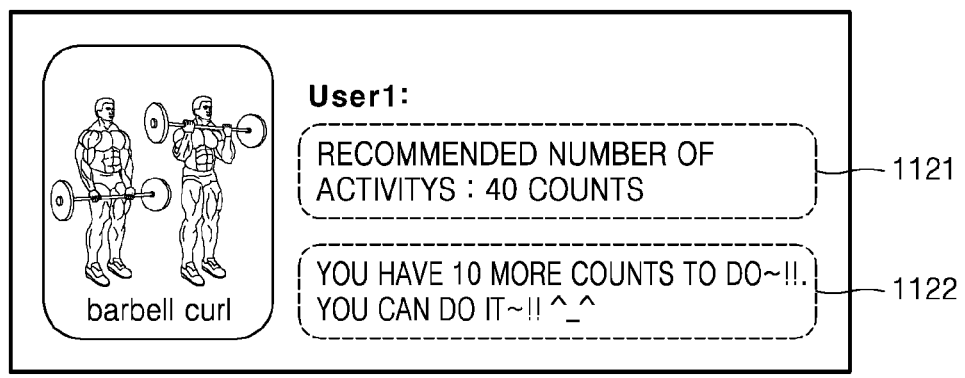
FIGS. 12 and 13 illustrate examples in which activity (e.g., exercise) coaching information is displayed, according to exemplary embodiments.
Figure 13:
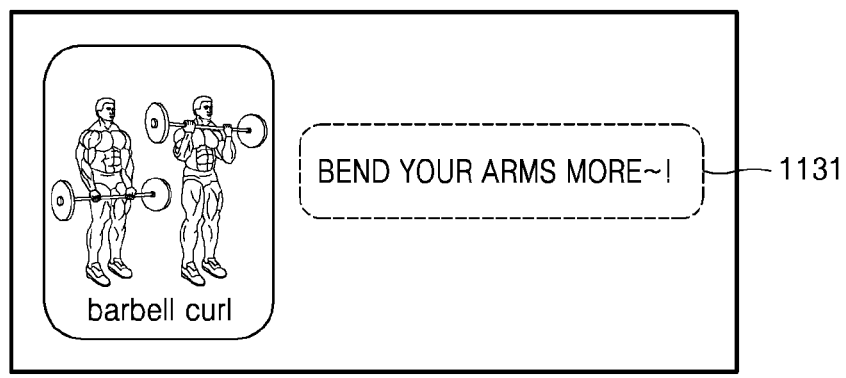

FIGS. 12 and 13 illustrate examples in which activity (e.g., exercise) coaching information is displayed, according to exemplary embodiments.

Based on physical information of a user which is received from the wearable device 200, the controller 130 of the device 100 may display, on the display unit 121, exercise coaching information according to an activity type of the user.

For example, as illustrated in FIG. 12, when the user does barbell curl exercise, the controller 130 may provide, on the display unit 121, information about the recommended number of exercises (e.g., "recommended number of exercises: 40 counts" 1121), based on information about the number of exercises which is received from the wearable device 200 worn on a user's body.

Based on the information about the number of exercises of the user, the controller 130 may display a cheering message (e.g., "You have 10 more counts to do~!!, You can do it~!! ^-^" 1122) on the display unit 121.

As illustrated in FIG. 13, based on movement pattern information of the wearable device 200 which is received from the wearable device 200, the controller 130 may display a message about a recommended posture (e.g., "Bend your arms more~!" 1131) on the display unit 121.

According to an exemplary embodiment, the controller 130 may provide the exercise coaching information, based on identification information of the user. For example, the controller 130 may determine the recommended number of exercises which is appropriate for the user, according to exercise history information of the user, the physical information of the user, or the like.

Figure 14:
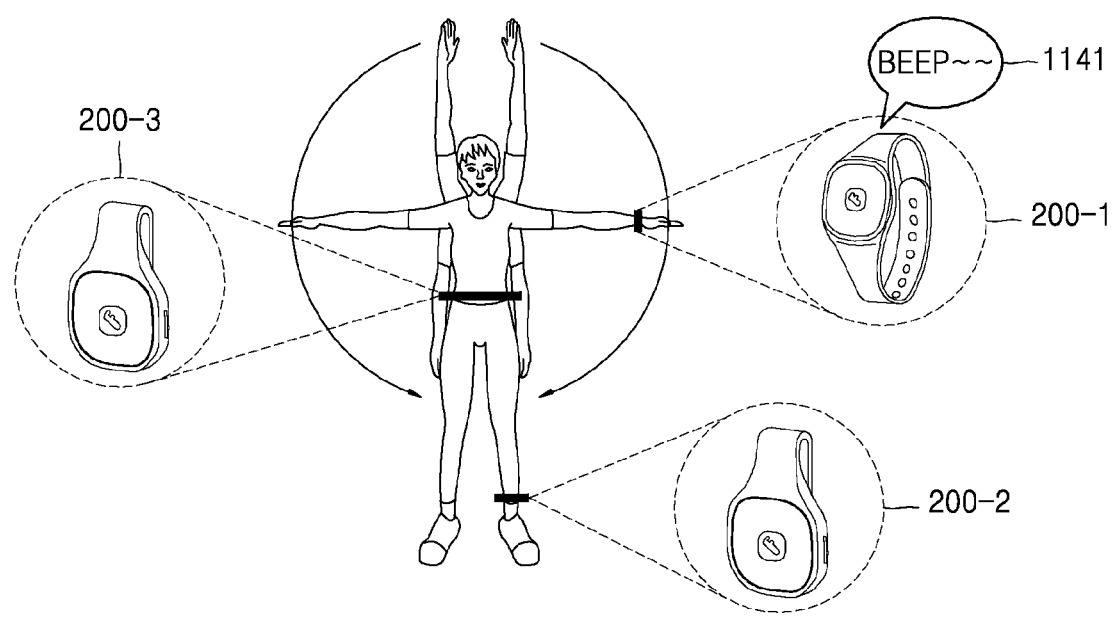
FIG. 14 illustrates an example in which an alarm is output based on battery remains, according to an exemplary embodiment.

FIG. 14 illustrates an example in which an alarm is output based on battery remains, according to an exemplary embodiment.

As illustrated in FIG. 14, when the battery charge of the main controlled-device 200-1 is less than a preset reference charge, the controller 130 of the device 100 may control the main controlled-device 200-1 to output a preset alarm (e.g., an audible beep sound 1141) so as to indicate the remaining battery charge.

When the battery remains is less than the preset reference charge, a controller 230 (refer to FIG. 21) of the wearable device 200 may output a preset alarm via a sound output unit (not shown).

According to the present exemplary embodiment, while the user is doing an arm exercise, when the user hears the alarm indicating insufficient battery charge remains for the main controlled-device 200-1 that is worn on a wrist of the user, the user may change from the wearable device 200-1 worn on the wrist to the wearable device 200-1 that is worn on an ankle of the user that has sufficient battery charge remaining, and thus may effectively continue to measure physical variation according to the arm exercise.

According to the present exemplary embodiment, when the battery remains of the main controlled-device 200-1 is less than the preset reference, the controller 130 of the device 100 may re-determine a main controlled-device from among the second and third wearable devices 200-2 and 200-3 that are worn on the user's body.

The controller 130 of the device 100 may control, via the communicator 150, a wearable device, which is re-determined as the main controlled-device, to obtain physical information of the user.

For example, when it is difficult to measure an amount of activity (e.g., exercise) of the user due to the insufficient battery charge remains for the main controlled-device 200-1, the controller 130 of the device 100 may re-determine a device at a more appropriate wearing position as a main controlled-device, wherein the device is from among the second and third wearable devices 200-2 and 200-3, and thus may continue to measure an amount of activity (e.g., exercise) of the user.

Figure 15:
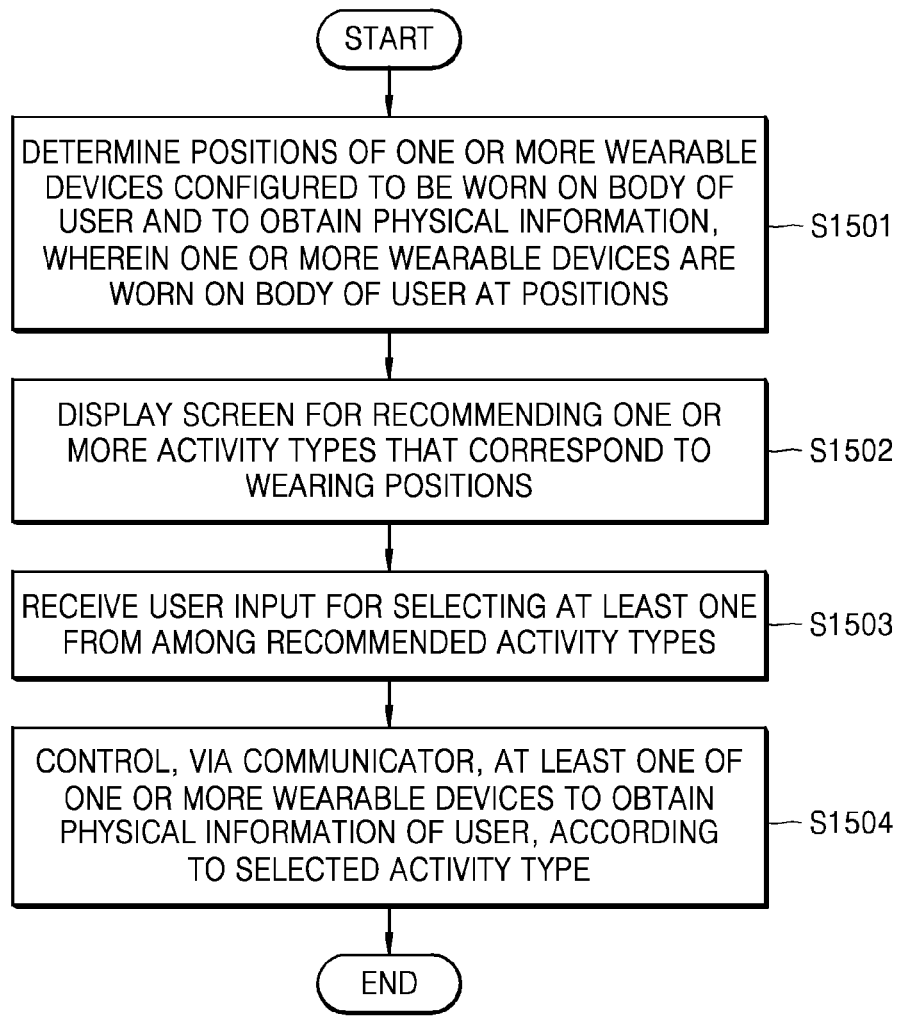
FIG. 15 is a flowchart illustrating a second exemplary embodiment.
Figure 16:
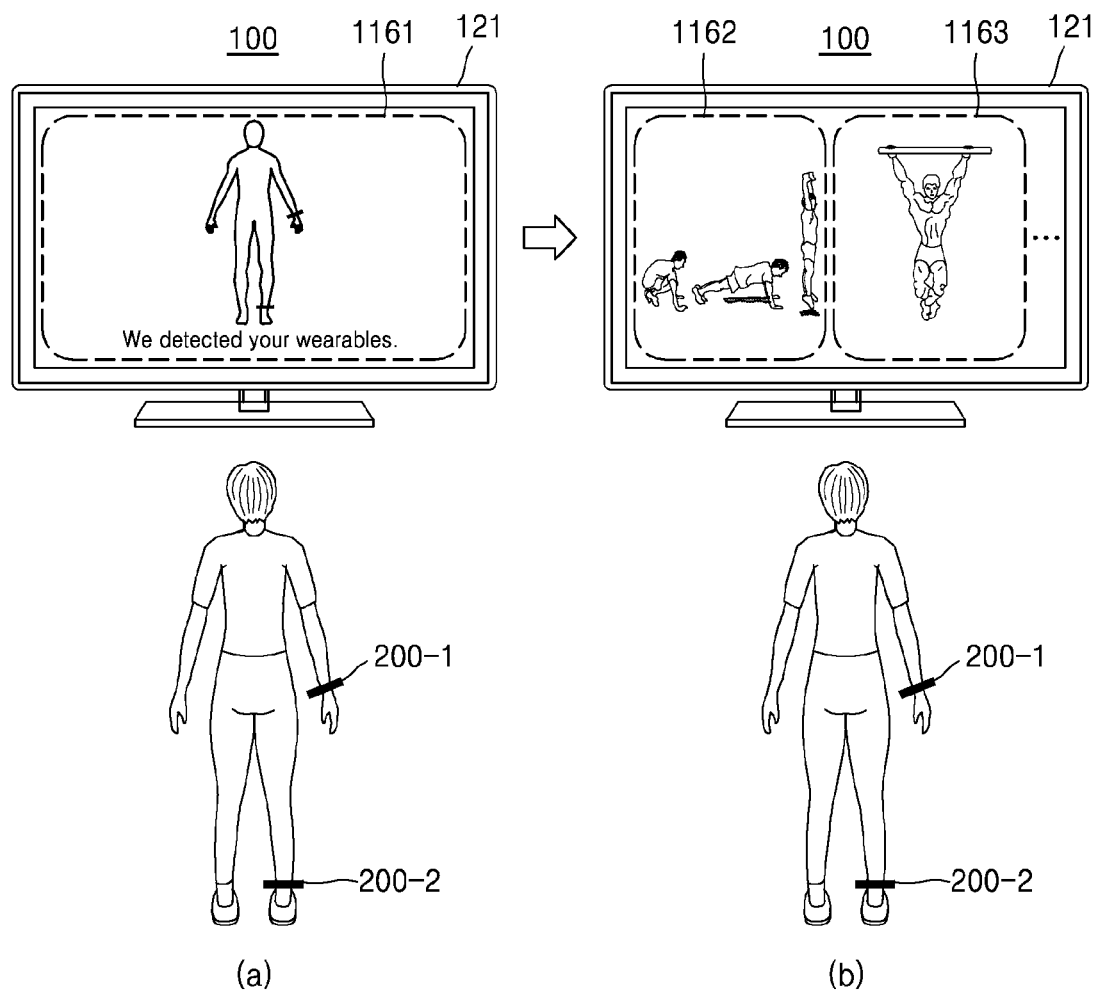
FIG. 16 illustrates the second exemplary embodiment.

FIG. 15 is a flowchart illustrating another exemplary embodiment. FIG. 16 illustrates the exemplary embodiment of FIG. 15.

According to an exemplary embodiment, when a user wears at least one wearable device on a user's body, the device 100 may recommend an activity (e.g., exercise) program that is appropriate for measuring an amount of activity, physical variation, or the like at a wearing position of the wearable device.

For example, when the device 100 determines that the user has worn the wearable device on an arm of the user, the device 100 may display, on the display unit 121, a recommendation list of activity (e.g., exercise) that highly require arm movements.

In operation S1501 of FIG. 15, the controller 130 of the device 100 may determine positions of one or more wearable devices configured to be worn on a user's body and to obtain physical information, wherein the one or more wearable devices are worn on the user's body at the positions.

As illustrated in an exemplary embodiment of (a) of FIG. 16, the controller 130 of the device 100 may determine wearing positions of the first and second wearable devices 200-1 and 200-2 that a user wears, and may display a screen 1161 indicating the wearing positions on the display unit 121.

A method of determining a wearing position of a wearable device, the method being performed by the device 100, is described above with reference to, and apparent from, FIGS. 3 through 6, thus, further descriptions thereof are omitted here.

In operation S1502 of FIG. 15, the controller 130 of the device 100 may display, on the display unit 121, a screen for recommending one or more activity (e.g., exercise) types that correspond to the wearing positions of the one or more wearable devices.

As illustrated in (b) of FIG. 16, when the device 100 determines that the user has worn the first and second wearable devices 200-1 and 200-2 on his/her wrist and ankle, the device 100 may display, on the display unit 121, screens 1162 and 1163 for recommending activity programs that mainly use hands, arms, feet, and legs.

A method of recommending an activity type corresponding to a wearing position of the wearable device 200, the method being performed by the device 100, is described above with reference to, and apparent from, FIG. 8, thus, further descriptions thereof are omitted here.

In operation S1503 of FIG. 15, the controller 130 of the device 100 may receive a user input for selecting at least one from among the recommended activity (e.g., exercise) types.

For example, the user input may include, but is not limited to, a user's touch input with respect to a touch screen, and receiving, via short-distance communication, a control signal according to operation of a remote controller.

In operation S1504 of FIG. 15, the controller 130 of the device 100 may control, via the communicator 150, at least one of the one or more wearable devices to obtain physical information of the user, according to the selected activity type.

For example, when push-up exercise is selected, the device 100 may control the first wearable device 200-1, which is worn on the wrist of the user, to obtain the number of exercises, a pulse rate, calorie consumption, or the like of the user.

Figure 17:
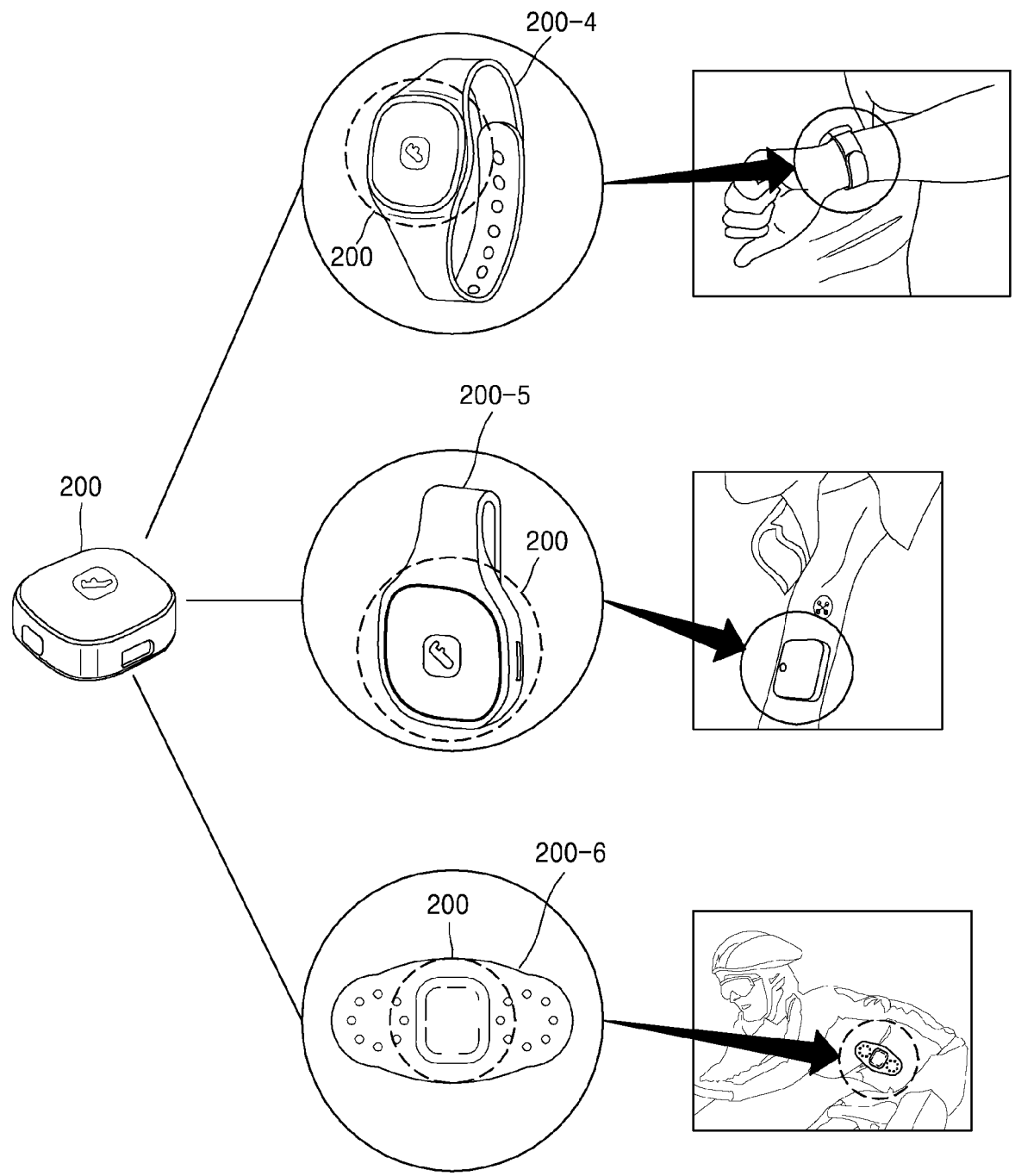
FIG. 17 illustrates an example in which wearable devices are worn, according to exemplary embodiments.
Figure 18:
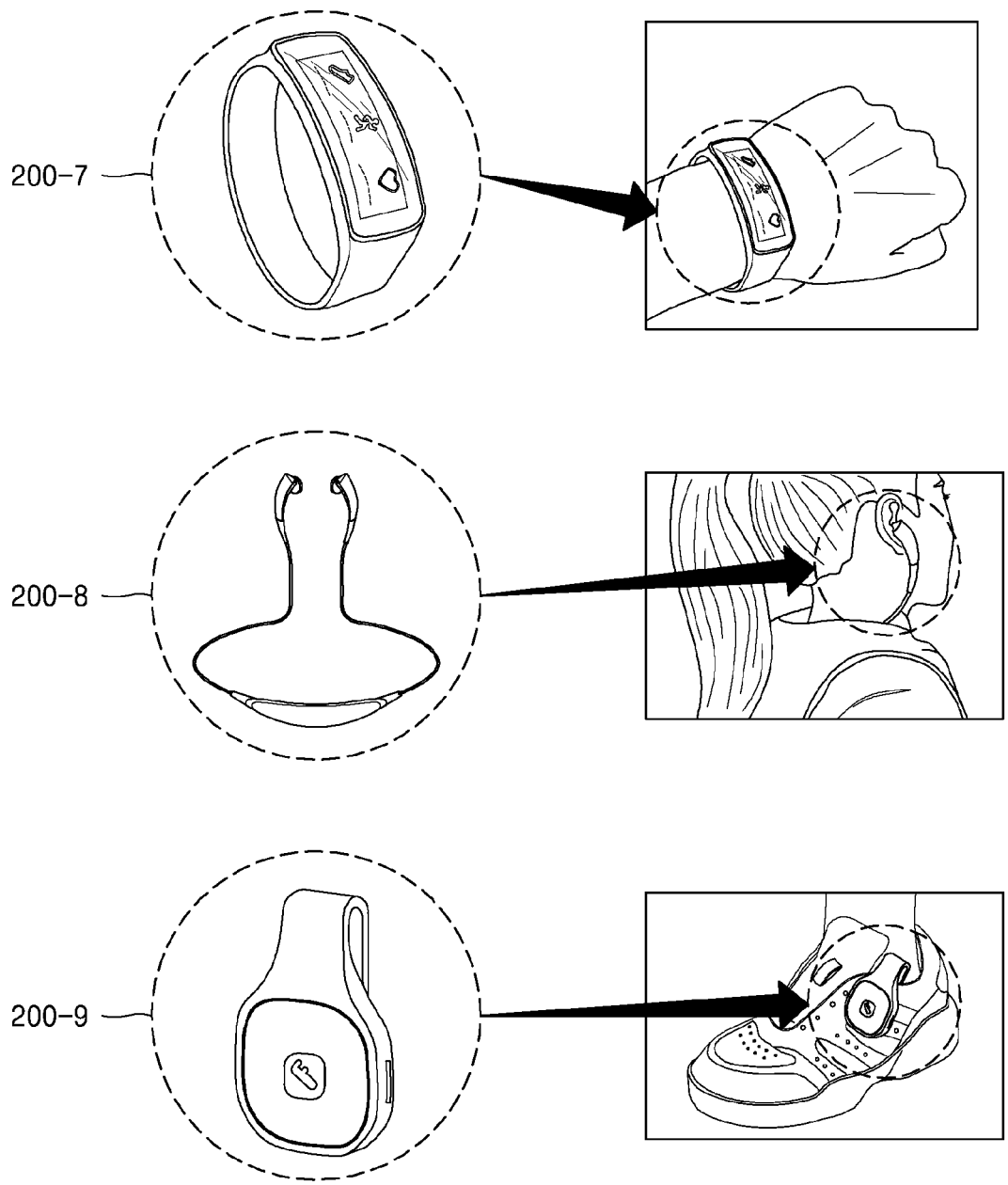
FIG. 18 illustrates an example in which wearable devices are worn, according to exemplary embodiments

FIGS. 17 and 18 illustrate examples of wearing locations in which wearable devices may be worn, according to exemplary embodiments. Other wearing locations are contemplated.

FIG. 17 illustrates an example of the wearable device 200 that is wearable on different parts of a body. For example, as illustrated in FIG. 17, the wearable device 200 that obtains physical information may be combined with a wrist-wearable band of a user and thus may be used as a watch-type wearable device 200-4. The wearable device 200 may be also combined with a clip that is attachable to clothes or shoes of the user and thus may be used as a clip-type wearable device 200-5. The wearable device 200 may be combined with a patch that is attachable to a user's body and thus may be used as a patch-type wearable device 200-6.

FIG. 18 illustrates examples of wearable devices that are configured to be worn on or around particular parts of a body. For example, as illustrated in FIG. 18, a wearable device 200-7 that obtains physical information may be a band-type wearable device that is wearable on a wrist of a user. A wearable device 200-8 that obtains physical information may be an earphone-type wearable device that is wearable on a neck of the user. Also, a wearable device 200-9 that obtains physical information may be a clip-type wearable device that is attachable to clothes or shoes of the user.

The one or more exemplary embodiments should be considered in a descriptive sense only and not for purposes of limitation, and are not limited to an order of the operations in the flowcharts of FIGS. 2, 3, 7, 9, and 15. According to other exemplary embodiments, some operations may be skipped or added, and an order of some operations may be changed.

Figure 19:
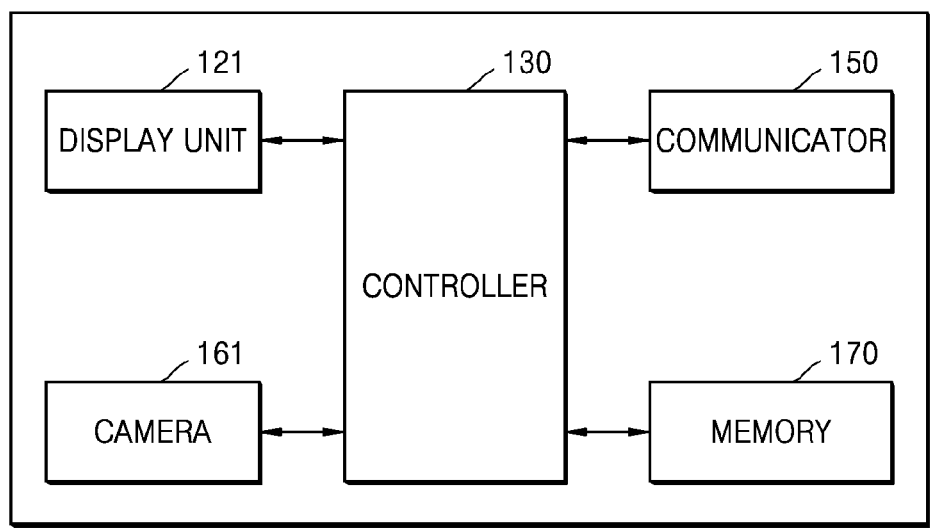
FIG. 19 is a block diagram of a device, according to exemplary embodiments.
Figure 20:
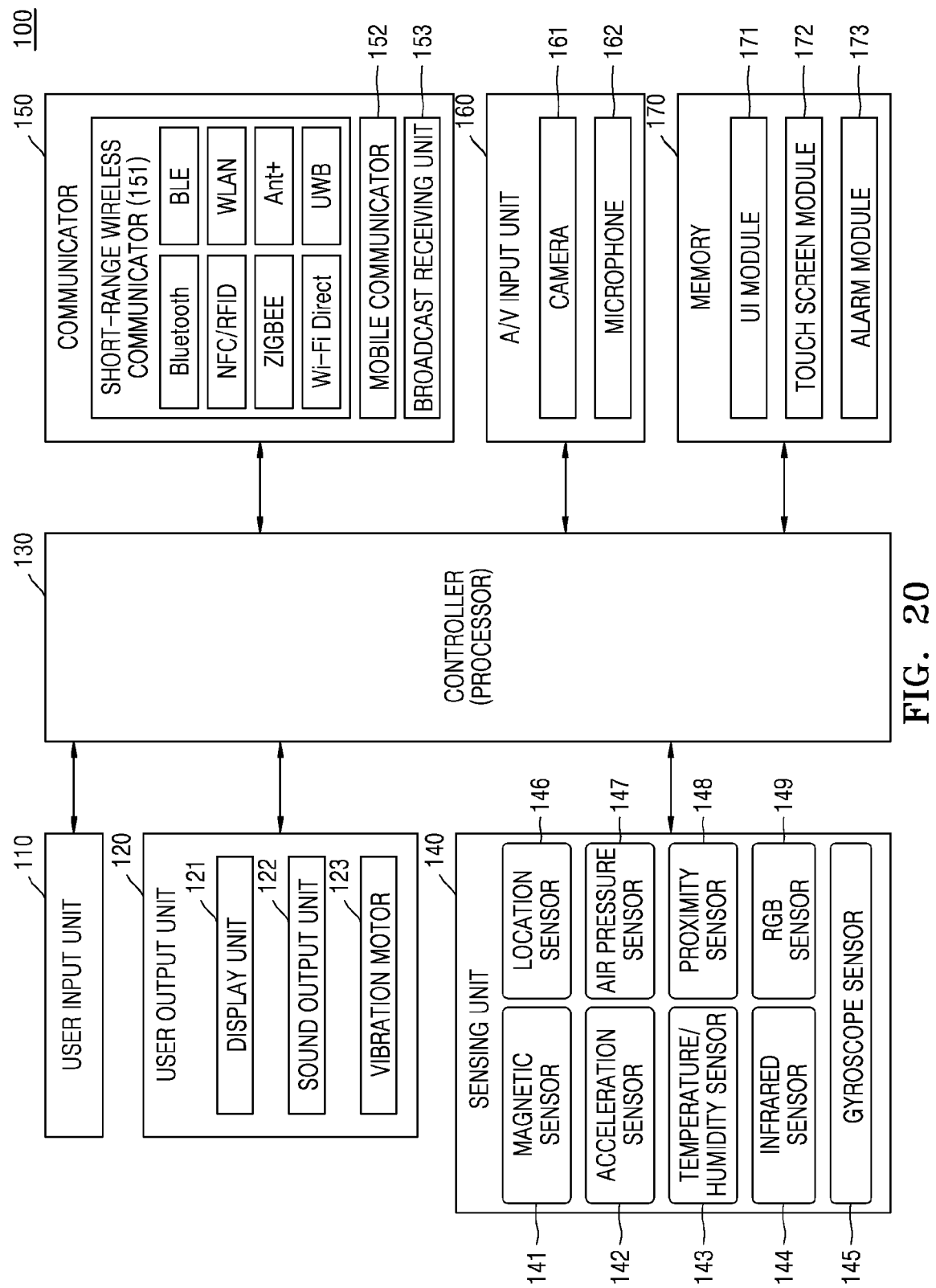
FIG. 20 is a block diagram of a device, according to exemplary embodiments.

FIGS. 19 and 20 are block diagrams illustrate aspects of the device 100, according to exemplary embodiments.

Referring to FIG. 19, the device 100 may include the display unit 121, the communicator 150, the camera 161, the memory 170, and the controller 130. However, not all elements shown in FIG. 19 are necessary elements of the device 100. That is, the device 100 may be embodied with more or less elements than the elements shown in FIG. 19.

For example, as illustrated in FIG. 20, the device 100 may further include a user input unit 110, an output unit 120, the sensing unit 140, and an audio/video (A/V) input unit 160, in addition to the display unit 121, the communicator 150, the camera 161, the memory 170, and the controller 130.

The user input unit 110 may indicate a unit by which a user inputs data so as to control the device 100. For example, the user input unit 110 may include a key pad, a dome switch, a touch pad (a touch capacitive type touch pad, a pressure resistive type touch pad, an infrared beam sensing type touch pad, a surface acoustic wave type touch pad, an integral strain gauge type touch pad, a piezo effect type touch pad, or the like), a jog wheel, and a jog switch, but one or more embodiments are not limited thereto.

The user input unit 110 may include an external apparatus capable of delivering a control signal via wired or wireless communication using the communicator 150. For example, the external apparatus may include a mouse, a keyboard, a remote controller, or the like.

The user input unit 110 may receive a user input by being controlled by the controller 130. For example, the user input unit 110 may receive a user input for selecting at least one of activity (e.g., exercise) types recommended on the display unit 121.

The output unit 120 may output an audio signal, a video signal, or a vibration signal by being controlled by the controller 130, and may include the display unit 121, a sound output unit 122, a vibration motor 123, or the like.

The display unit 121 displays information that is processed in the device 100, by being controlled by the controller 130.

For example, the display unit 121 may display a screen for recommending a preset activity type that corresponds to a position at which a wearable device is worn on a user's body.

Also, the display unit 121 may display physical information of the user which is obtained by a main controlled-device.

Also, for example, the display unit 121 may display exercise coaching information according to an exercise type, based on the physical information of the user.

Also, the display unit 121 may display a screen for guiding a movement pattern so as to determine wearing positions of one or more wearable devices that are worn on the user's body.

When the display unit 121 and a touch pad form a mutual layer structure and then are formed as a touch screen, the display unit 121 may be used as both an output device and input device. The display unit 121 may include at least one of liquid crystal display (LCD), a thin film transistor-liquid crystal display (TFT-LCD), an organic light-emitting diode (OLED) display, a flexible display, a three-dimensional (3D) display, and an electrophoretic display. According to a type of the device 100, the device 100 may include at least two display units 121. Here, the at least two display units 121 may be disposed to face each other by using a hinge.

The sound output unit 122 may output audio data that is received from the communicator 150 or is stored in the memory 170. The sound output unit 122 may also output a sound signal (e.g., a call signal receiving sound, a message receiving sound, a notifying sound, or the like) related to capabilities performed by the device 100. The sound output unit 122 may include a speaker, a buzzer, or the like.

The vibration motor 123 may output a vibration signal. For example, the vibration motor 123 may output the vibration signal that corresponds to an output of the audio data (e.g., the call signal receiving sound, the message receiving sound, or the like) or video data. When a touch is input to the touch screen, the vibration motor 123 may output a vibration signal.

The controller 130 may generally control all operations of the device 100. For example, the controller 130 may control the user input unit 110, the output unit 120, the sensing unit 140, the communicator 150, the A/V input unit 160, etc. by executing programs stored in the memory 170.

The controller 130 according to an exemplary embodiment may determine the wearing positions of one or more wearable devices that are worn on the user's body.

Also, the controller 130 may determine the activity (e.g., exercise) type of the user.

Also, the controller 130 may determine at least one wearable device as a main controlled-device, wherein the at least one wearable device corresponds to the activity (e.g., exercise) type of the user and is from among the one or more wearable devices that are worn on the user's body, based on the wearing positions.

Also, the controller 130 may differently control, from among the one or more wearable devices that are worn on the user's body, the main controlled-device from wearable devices excluding the main controlled-device, via the communicator 150.

Also, the controller 130 may determine the activity type of the user, based on a user input for selecting, via the user input unit 110, at least one from among the recommended activity types.

Also, the controller 130 may receive movement pattern information of the wearable device for a preset time period via the communicator 150, and may determine the activity type of the user, based on the received movement pattern information.

Also, the controller 130 may control power of the wearable devices to be turned off, wherein the wearable devices exclude the main controlled-device and are from among the one or more wearable devices that are worn on the user's body.

Also, the controller 130 may receive, via the communicator 150, physical information of the user which is obtained from the main controlled-device, and may display the received physical information of the user on the display unit 121.

Based on the received physical information of the user, the controller 130 may display activity coaching information according to the activity type on the display unit 121.

When battery remains of the main controlled-device is less than a preset reference, the controller 130 may control the main controlled-device to output a preset alarm so as to indicate the battery remains.

Also, the controller 130 may receive, via the communicator 150, movement pattern information of the one or more wearable devices respectively from the one or more wearable devices worn on the user's body.

The controller 130 may compare the received movement pattern information with movement pattern information stored in the memory 170, and may determine a wearing position that corresponds to the received movement pattern information.

The controller 130 may display a screen for guiding a movement pattern so as to determine a wearing position of the at least one wearable device worn on the user's body.

The controller 130 may receive, via the communicator 150, a plurality of pieces of information about the wearing positions of the one or more wearable devices, respectively from the one or more wearable devices worn on the user's body.

The controller 130 may determine positions at which the one or more wearable devices are worn on the user's body, by referring to an image that is obtained by the camera 161 and that may include the user.

The controller 130 may detect, via the camera 161, a spectrum emitted from the at least one wearable device, and may determine the position at which the at least one wearable device is worn on the user's body.

The controller 130 may control, via the communicator 150, the at least one wearable device to obtain physical information of the user according to the activity (e.g., exercise) type selected via the user input unit 110.

The sensing unit 140 may sense a state of the device 100 or a status around the device 100 and may transfer sensed information to the controller 130. The sensing unit 140 may include at least one selected from a magnetic sensor 141, an acceleration sensor 142, a temperature/humidity sensor 143, an infrared sensor 144, a gyroscope sensor 145, a location/position sensor (e.g., a global positioning system (GPS)) 146, an air pressure sensor 147, a proximity sensor 148, and an RGB sensor (i.e., a luminance sensor) 149, but one or more exemplary embodiments are not limited thereto. Functions of the sensors may be intuitionally deduced by one of ordinary skill in the art by referring to names of the sensors, and thus, detailed descriptions thereof are omitted here.

The sensing unit 140 may include a sensor for sensing a touch input via an input instrument, and a sensor for sensing a touch input by a user. In this case, the sensor for sensing the touch input by the user may be included in the touch screen or the touch pad. The sensor for sensing the touch input via the input instrument may be formed below or in the touch screen or the touch pad.

The communicator 150 may include one or more elements allowing communication between the device 100 and an external device or between the device 100 and a server (not shown). For example, the communicator 150 may include a short-range wireless communicator 151, a mobile communicator 152, and a broadcast receiving unit 153.

The short-range wireless communicator 151 may include, but is not limited to, a Bluetooth communicator, a Bluetooth Low Energy (BLE) communicator, a near field communication (NFC) unit, a WLAN (Wi-Fi) communicator, a ZigBee communicator, an infrared Data Association (IrDA) communicator, a Wi-Fi Direct (WFD) communicator, a ultra wideband (UWB) communicator, or an Ant+ communicator.

The mobile communicator 152 exchanges a wireless signal with at least one of a base station, an external terminal, and a server on a mobile communication network. The wireless signal may include various types of data according to communication of a sound call signal, a video call signal, or a text/multimedia message.

The broadcast receiving unit 153 receives a broadcast signal and/or information related to a broadcast from the outside through a broadcast channel. The broadcast channel may include a satellite channel and a ground wave channel. In another embodiment, the device 100 may not include the broadcast receiving unit 153.

The A/V input unit 160 may receive an input of an audio signal or a video signal and may include the camera 161 and a microphone 162. The camera 161 may obtain an image frame such as a still image or a moving picture via an image sensor during a video call mode or an image-capturing mode. An image that is captured via the image sensor may be processed by the controller 130 or a separate image processing unit (not shown).

The image frame that is processed by the camera 161 may be stored in the memory 170 or may be transmitted to an external source via the communicator 150. According to a configuration of the device 100, two or more cameras 161 may be arranged. In another exemplary embodiment, the camera 161 may be embodied as an apparatus separated from the device 100, and may be electrically connected with the device 100.

The camera 161 may sense a predefined spectrum (ultraviolet rays, infrared rays, etc.). The microphone 162 receives an input of an external sound signal and processes the received sound signal into electrical voice data. For example, the microphone 162 may receive a sound signal from an external device or a speaker. In order to remove noise that occurs while the sound signal is externally input, the microphone 162 may use various noise removing algorithms.

The memory 170 may store a program for processing and controlling the controller 130, and may store a plurality of pieces of data that are input to or output from the device 100.

The memory 170 may include a storage medium of at least one type selected from a flash memory, a hard disk, a multimedia card type memory, a card type memory such as a secure digital (SD) or xD-Picture (xD) card memory, a random access memory (RAM), a static random access memory (SRAM), a read-only memory (ROM), an electrically erasable programmable read-only memory (EEPROM), a programmable read-only memory (PROM), a magnetic memory, a magnetic disc, and an optical disc. The device 100 may run web storage or a cloud server that performs a storage function of the memory 170 on the Internet.

The programs stored in the memory 170 may be classified into a plurality of modules according to their functions, for example, into a user interface (UI) module 171, a touch screen module 172, an alarm module 173, etc.

The UI module 171 may provide a specialized UI or graphical user interface (GUI) in connection with the device 100 for each application. The touch screen module 172 may detect a user's touch gesture on the touch screen and transmit information related to the touch gesture to the controller 130. The touch screen module 172 may recognize and analyze a touch code. The touch screen module 172 may be configured by additional hardware including a controller.

Various sensors may be arranged in or near the touch screen so as to detect a touch or a proximate touch on the touch sensor. An example of the sensor to detect the touch on the touch screen may include a tactile sensor. The tactile sensor detects a contact of a specific object at least as sensitively as a person can detect. The tactile sensor may detect various types of information such as the roughness of a contact surface, the hardness of the contact object, the temperature of a contact point, or the like.

An example of the sensor to detect the touch on the touch screen may include a proximity sensor. The proximity sensor detects the existence of an object that approaches a predetermined detection surface or that exists nearby, by using a force of an electro-magnetic field or an infrared ray, instead of a mechanical contact. Examples of the proximity sensor include a transmission-type photoelectric sensor, a direction reflection-type photoelectric sensor, a mirror reflection-type photoelectric sensor, a high frequency oscillation-type proximity sensor, a capacity-type proximity sensor, a magnetic proximity sensor, an infrared-type proximity sensor, or the like. The touch gesture of the user may include a tap gesture, a touch & hold gesture, a double tap gesture, a drag gesture, a panning gesture, a flick gesture, a drag & drop gesture, a swipe gesture, or the like.

The alarm module 173 may generate a signal for notifying the user about an occurrence of an event in the device 100. Examples of the event that may occur in the device 100 include a call signal receiving event, a message receiving event, a key signal input event, a schedule notifying event, or the like. The alarm module 173 may output an alarm signal in the form of a video signal via the display unit 121, an alarm signal in the form of an audio signal via the sound output unit 122, or an alarm signal in the form of a vibration signal via the vibration motor 123.

FIG. 21 is a block diagram of the wearable device 200, according to an exemplary embodiment.

As illustrated in FIG. 21, the wearable device 200 according to the present exemplary embodiment may include the communicator 250, a memory 270, a display unit 221, the sensing unit 240, and the controller 230. However, not all elements shown in FIG. 21 are necessary elements of the wearable device 200. That is, the wearable device 200 may be embodied with more or less elements than the elements shown in FIG. 21.

The controller 230 may generally control all operations of the wearable device 200. In more detail, the controller 230 of the wearable device 200 according to the present exemplary embodiment may detect a movement pattern of the wearable device 200 by using the sensing unit 240.

The controller 230 of the wearable device 200 according to the present exemplary embodiment may transmit, to the device 100 via the communicator 250, information about the movement pattern of the wearable device 200 which is obtained by using the sensing unit 240.

The communicator 250 may include one or more elements allowing communication between the wearable device 200 and an external device. For example, the communicator 250 may include a short-range wireless communicator (not shown), a mobile communicator (not shown), and a broadcast receiving unit (not shown).

The memory 270 may store a program for processing and controlling the controller 230, and may store a plurality of pieces of data that are input to or output from the wearable device 200.

The sensing unit 240 may include at least one selected from a magnetic sensor (not shown) an acceleration sensor (not shown), a temperature/humidity sensor (not shown), an infrared sensor (not shown), a gyroscope sensor (not shown), a position sensor (e.g., a GPS) (not shown), an air pressure sensor (not shown), a proximity sensor (not shown), and an RGB sensor (i.e., a luminance sensor) (not shown), but one or more exemplary embodiments are not limited thereto. Functions of the sensors may be intuitionally deduced by one of ordinary skill in the art by referring to names of the sensors, and thus, more descriptions thereof are omitted here.

The sensing unit 240 according to the present exemplary embodiment may sense a movement of the wearable device 200, and physical variation, an amount of activity (e.g., exercise), a biological signal, or the like of a user's body who wears the wearable device 200.

The wearable device 200 according to the present exemplary embodiment may further include a sound output unit (not shown).

The sound output unit may output audio data that is received from the communicator 250 or is stored in the memory 270. The sound output unit may also output a sound signal (e.g., a call signal receiving sound, a message receiving sound, a notifying sound, or the like) related to capabilities performed by the wearable device 200. The sound output unit may include a speaker, a buzzer, or the like.

When battery charge remains is less than a preset reference charge, the sound output unit of the wearable device 200 according to the present exemplary embodiment may output a preset alarm so as to indicate the battery charge that remains.

Figure 22:
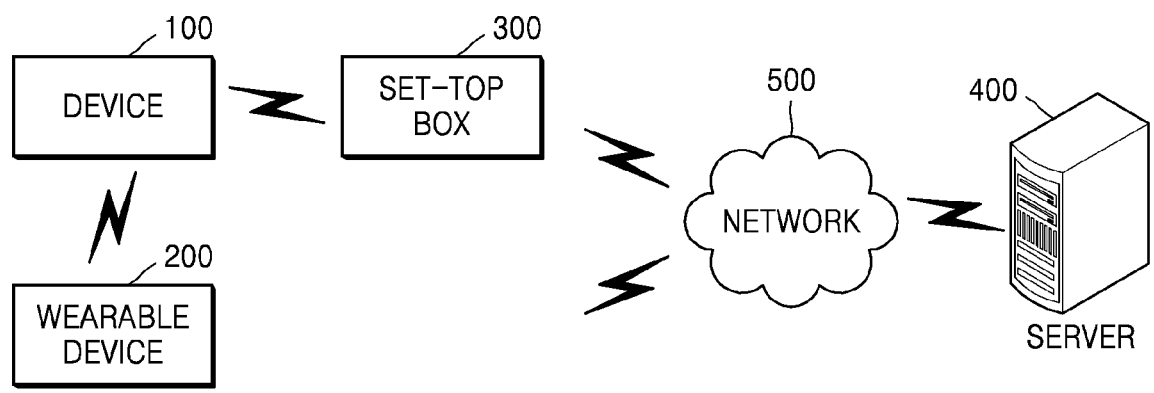
FIG. 22 illustrates a configuration of a system, according to an exemplary embodiment.

FIG. 22 illustrates a configuration of a system, according to an exemplary embodiment.

Referring to FIG. 22, the system according to the present exemplary embodiment may include at least one of the device 100, the wearable device 200, a set-top box 300, and a server 400 which may communicate with each other via a network 500. For example, the system may include the device 100 and the set-top box 300. As another example, the system may include the device 100 and the server 400.

The network 500 may indicate a telecommunication network. The telecommunication network may include, but is not limited to, at least one of a computer network, Internet, the Internet of Things (IoT), and a telephone network.

According to the present exemplary embodiment, the device 100 may be embodied as an analog TV, a digital TV, a 3D-TV, a smart TV, a light-emitting diode (LED) TV, an OLED TV, a plasma TV, a monitor, or the like, and it is obvious to one of ordinary skill in the art that examples of the device 100 are not limited thereto.

The set-top box 300 according to the present exemplary embodiment indicates a terminal that includes a communicator (not shown) and a processor (not shown) and is connected to an external network so as to provide a multimedia communication service.

In addition, the set-top box 300 according to the present exemplary embodiment may include a camera (not shown). The camera included in the set-top box 300 may obtain an image frame such as a still image or a moving picture via an image sensor. According to the present exemplary embodiment, the camera included in the set-top box 300 may obtain the image frame including an image of a user.

While it is described that the controller 130 of the device 100 performs the exemplary embodiments described in the specification, the disclosure is not limited thereto. In some exemplary embodiments, the set-top box 300 may perform a function supposed to be performed by the controller 130 of the device 100, and may transmit a result of the performance to the device 100. In this regard, the device 100 may display, on the display unit 121, information processed by the set-top box 300.

According to the present exemplary embodiment, the system may include the server 400. The server 400 may communicate with at least one of the device 100, the wearable device 200, and the set-top box 300 via the network.

The server 400 according to the present exemplary embodiment may update information about a new activity type, activity coaching information, or the like, and may provide the information, the activity coaching information, or the like to the device 100 or the set-top box 300.

In addition, the server 400 according to the present exemplary embodiment may store physical information, activity (e.g., exercise) history information, or the like according to each of a plurality of users, based on identification information of each user. Based on an activity history, physical information, fitness information, or the like of the user corresponding to the identification information, the server 400 may determine a level of difficulty of a recommendation-target activity type, and may provide an activity type appropriate for each user.

Figure 23:
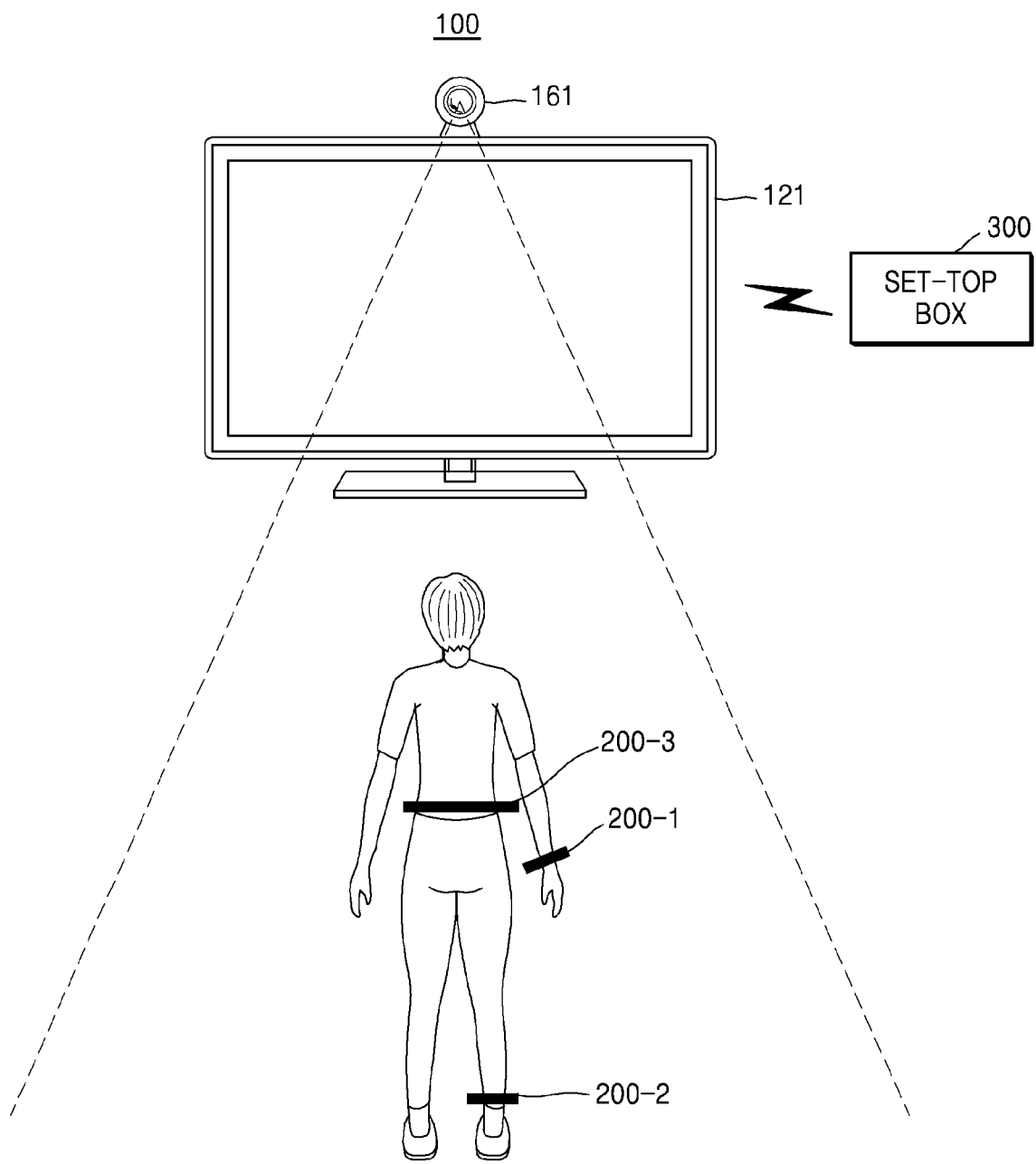
FIG. 23 illustrates the system, according to exemplary embodiments.
Figure 24:
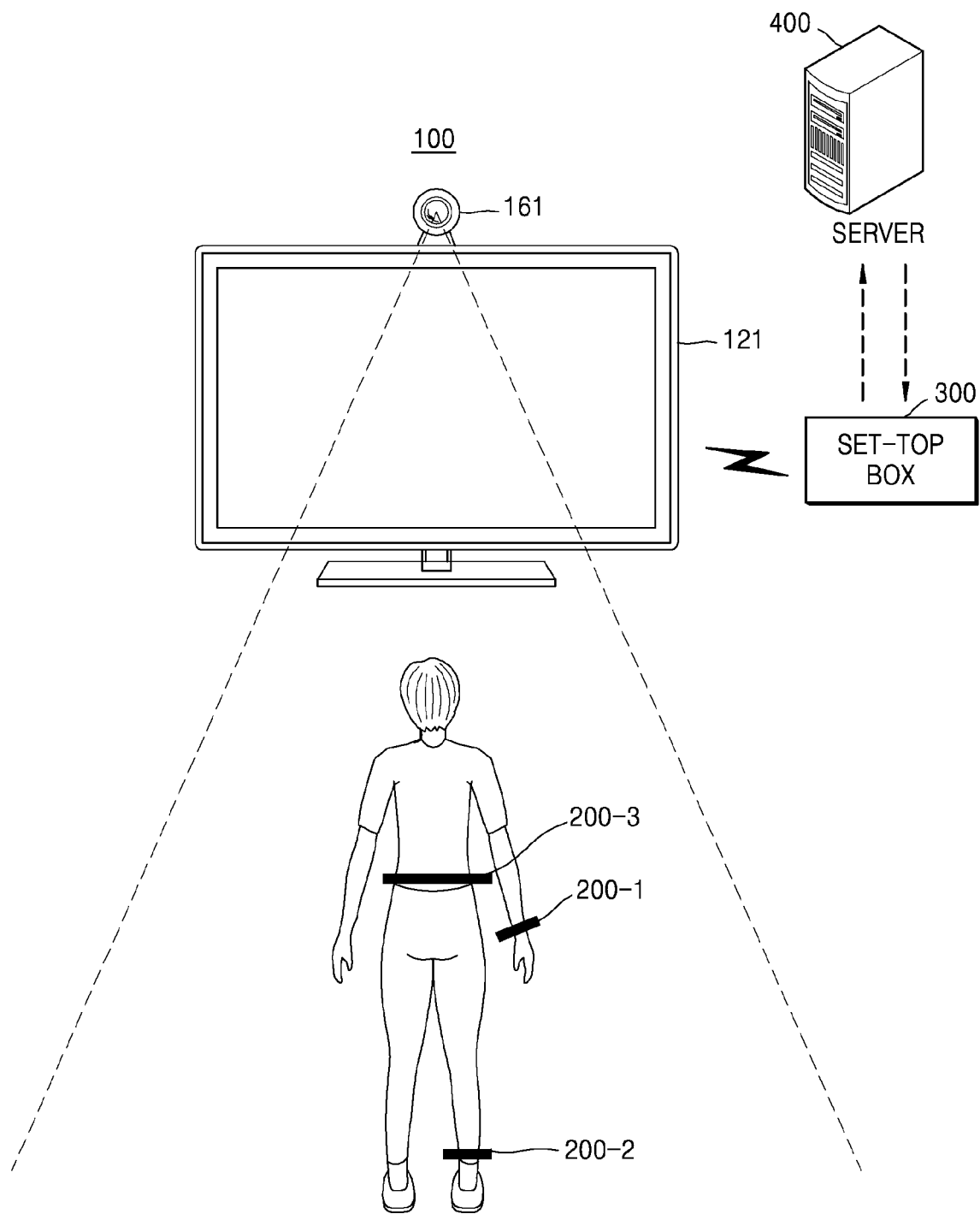
FIG. 24 illustrates the system, according to exemplary embodiments.

FIGS. 23 and 24 illustrate the system, according to exemplary embodiments.

Referring to FIG. 23, according to the present exemplary embodiment, the device 100 may receive information from the set-top box 300, and may display the received information on the display unit 121 of the device 100.

According to the present exemplary embodiment, the device 100 may recognize a face of a user via the camera 161, and may transmit identification information of the user to the set-top box 300. In another exemplary embodiment, the set-top box 300 may include a camera (not shown), and may recognize the face of the user via the camera (not shown).

According to the present exemplary embodiment, the set-top box 300 may manage a plurality of pieces of user information, based on a plurality of pieces of identification information. For example, the set-top box 300 may store the user information including activity (e.g., exercise) history information, physical information, or the like of a user, based on the identification information of the user.

According to the present exemplary embodiment, the set-top box 300 may determine and recommend an activity type appropriate for the user, based on the user information. For example, the set-top box 300 may determine, based on an activity history and fitness information of the user, a level of difficulty of an activity, an activity type, or the like which are appropriate for the user, and may transmit information about the determination result to the device 100. The device 100 may display, on the display unit 121, the information received from the set-top box 300.

Referring to FIG. 24, the set-top box 300 may receive information from the server 400, and may control the received information to be transmitted to the device 100 and then to be displayed on the display unit 121 of the device 100.

According to the present exemplary embodiment, the server 400 may manage user information, based on identification information of a user. According to the present exemplary embodiment, the user may access, by using another device (not shown), the user information stored in the server 400, based on a face image of the user or the identification information including log-in information (an ID, a password, etc.).

According to the present exemplary embodiment, the server 400 may manage information of various activity (e.g., exercise) types, information of a level of difficulty of an activity, information of a recommended activity type according to fitness information, information about recommended activity according to wearing positions where one or more wearable devices are worn on a user's body, or the like. For example, when the server 400 receives the identification information of the user from the set-top box 300, the server 400 may determine an appropriate activity type, based on an activity history, fitness information, or the like which correspond to the identification information, and may transmit information about a recommended activity type to the set-top box 300.

The one or more exemplary embodiments described herein may be applied to different exemplary embodiments of the inventive concept, and only some exemplary embodiments may be embodied or a plurality of exemplary embodiments may be combined and thus be embodied.

The one or more embodiments may be embodied as a recording medium, e.g., a program module to be executed in computers, which include computer-readable commands. The computer storage medium may include any usable medium that may be accessed by computers, volatile and non-volatile medium, and detachable and non-detachable medium. Also, the computer storage medium includes all volatile and non-volatile media, and detachable and non-detachable media which are technically implemented to store information including computer readable commands, data structures, program modules or other data. The communication medium includes computer-readable commands, a data structure, a program module, other data as modulation-type data signals such as carrier signals, or other transmission mechanism, and includes other information transmission mediums.

Throughout the specification, the term 'unit' may indicate a hardware component such as a processor or a circuit, and/or may indicate a software component that is executed by a hardware configuration such as a processor.

It should be understood that the exemplary embodiments described herein should be considered in a descriptive sense only and not for purposes of limitation. Descriptions of features or aspects within each embodiment should typically be considered as available for other similar features or aspects in other embodiments. For example, configuring elements that are singular forms may be executed in a distributed fashion, and also, configuring elements that are distributed may be combined and then executed.

While one or more exemplary embodiments have been described with reference to the figures, it will be understood by those of ordinary skill in the art that various changes in form and details may be made therein without departing from the spirit and scope as defined by the following claims.

What is claimed is:

1. A device comprising:
   a communicator comprising communication circuitry;
   a memory for storing instructions; and
   a controller configured to execute the stored instructions to at least:
      receive, via the communicator, a plurality of pieces of movement pattern information of a plurality of wearable sensors, respectively from the plurality of wearable sensors configured to be simultaneously worn on a user's body;
      compare the received plurality of pieces of movement pattern information of the plurality of wearable sensors with movement pattern information which is pre-stored in the memory,
      based on a result of the comparing, determine wearing positions that correspond to each of the received plurality of pieces of movement pattern information for each of the plurality of wearable sensors,
      determine a type of activity being performed by the user, based on the received plurality of pieces of movement pattern information,
      determine a main controlled-device that is a single one of the plurality of wearable sensors that corresponds to the determined type of activity for measuring an amount of the activity being performed by the user, from among the plurality of wearable sensors, based on the determined wearing positions for each of the plurality of wearable sensors,
      control, via the communicator, the determined single main controlled-device that is a single one of the plurality of wearable sensors to operate for measuring the amount of the activity being performed by the user, and
      control, via the communicator, to turn off the plurality of wearable sensors excluding the determined main controlled-device that is the single one of the plurality of wearable sensors.

2. The device of claim 1, further comprising a display unit, and wherein the controller is configured to execute the instruction further to display, on the display unit, a screen for recommending activity types corresponding to the wearing positions where the plurality of wearable sensors are worn on the user's body, and determine the activity type of the user, based on a user input for selecting at least one of the recommended activity types.

3. The device of claim 1, wherein the controller is configured to execute the instructions further to receive movement pattern information of the plurality of wearable sensors for a preset time period via the communicator, and determine the activity type of the user, based on the received movement pattern information.

4. The device of claim 1, wherein the controller is configured to execute the instructions further to control the plurality of wearable sensors excluding the main controlled-device to operate in a lower power consumption mode.

5. The device of claim 1, wherein the controller is configured to execute the instructions further to control a physical information obtaining function of the plurality of wearable sensors excluding the main controlled-device to be turned off.

6. The device of claim 1, wherein, the controller is configured to execute the instructions further to re-determine the main controlled-device from among the plurality of wearable sensors worn on the user's body when a remaining battery charge of the main controlled-device is less than a preset reference charge.

7. The device of claim 6, wherein the controller is configured to execute the instructions further to control, via the communicator, the wearable sensors to obtain physical information of the user when a wearable sensor is re-determined as the main controlled-device.

8. The device of claim 1, further comprising a display unit, and wherein the controller is configured to execute the instructions further to receive, via the communicator, the physical information of the user which is obtained from the main controlled device, and to display the physical information of the user on the display unit.

9. The device of claim 8, wherein the controller is configured to execute the instructions further to display, on the display unit, activity coaching information according to the activity type, based on the physical information of the user.

10. The device of claim 1, wherein the memory stores the wearing positions corresponding to movement patterns of the plurality of wearable sensors.

11. The device of claim 10, further comprising a display unit, and wherein the controller is configured to execute the instructions further to display, on the display unit, a screen for guiding a movement pattern for determining the wearing positions of the plurality of wearable sensors worn on the user's body.

12. The device of claim 1, wherein the controller is configured to execute the instructions further to receive, via the communicator, a plurality of pieces of information about the wearing positions of the plurality of wearable sensors, respectively from the plurality of wearable sensors worn on the user's body.

13. The device of claim 1, further comprising a camera, and
   wherein the controller is configured to execute the instructions further to determine the wearing positions of each of the plurality of wearable sensors worn on the user's body, by referring to an image comprising the user and obtained via the camera.

14. The device of claim 1, further comprising a camera for detecting a preset spectrum, and
   wherein the controller is configured to execute the instructions further to detect, by using the camera, a spectrum emitted from the plurality of wearable sensors, and to determine, based on the spectrum, wearing positions where the plurality of wearable sensors are worn on the user's body.

15. An operating method of a device, comprising:
- receiving a plurality of pieces of movement pattern information of a plurality of wearable sensors, respectively from a plurality of wearable sensors configured to be simultaneously worn on a user's body;
- comparing the received plurality of pieces of movement pattern information of the plurality of wearable sensors with movement pattern information which is pre-stored in the memory,
- based on a result of the comparing, determining wearing positions that correspond to each of the received plurality of pieces of movement pattern information for each of the plurality of wearable sensors,
- determining a type of activity being performed by the user, based on the received plurality of pieces of movement pattern information;
- determining a main controlled-device, that is a single one of the plurality of wearable sensors that that corresponds to the determined type of activity for measuring an amount of the activity being performed by the user, from among the plurality of wearable sensors, based on determined movements for each of the plurality of wearable sensors;
- controlling the determined main controlled-device, that is a single one of the plurality of wearable sensors, to operate for measuring the amount of the activity being performed by the user, and
- controlling the plurality of wearable sensors to turn off the plurality of wearable sensors excluding the determined main controlled-device that is the single one of the plurality of wearable sensors.

* * * * *